US008802693B1

(12) United States Patent
Gault et al.

(10) Patent No.: US 8,802,693 B1
(45) Date of Patent: Aug. 12, 2014

(54) AZAADAMANTANE DERIVATIVES AND METHODS OF USE

(75) Inventors: Laura M. Gault, Lake Forest, IL (US); Robert A. Lenz, Libertyville, IL (US); Ahmed A. Othman, Waukegan, IL (US)

(73) Assignee: AbbVie Inc., North Chicago, IL (US)

( * ) Notice: Subject to any disclaimer, the term of this patent is extended or adjusted under 35 U.S.C. 154(b) by 123 days.

(21) Appl. No.: 13/417,005

(22) Filed: Mar. 9, 2012

Related U.S. Application Data

(60) Provisional application No. 61/607,490, filed on Mar. 6, 2012, provisional application No. 61/594,262, filed on Feb. 2, 2012, provisional application No. 61/578,863, filed on Dec. 21, 2011, provisional application No. 61/545,943, filed on Oct. 11, 2011, provisional application No. 61/545,961, filed on Oct. 11, 2011, provisional application No. 61/451,079, filed on Mar. 9, 2011.

(51) Int. Cl.
*A61K 31/44* (2006.01)
*C07D 455/04* (2006.01)

(52) U.S. Cl.
CPC .................................. *C07D 455/04* (2013.01)
USPC ........................................................ 514/294

(58) Field of Classification Search
CPC ...................................................... C07D 455/04
USPC ........................................................ 514/294
See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2008/0167336 A1 * | 7/2008 | Schrimpf et al. | 514/294 |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2012/0245195 A1 | 9/2012 | Chen et al. | |

FOREIGN PATENT DOCUMENTS

| | | |
|---|---|---|
| WO | 9507271 A1 | 3/1995 |
| WO | 9710223 A1 | 3/1997 |
| WO | 2005099353 A2 | 10/2005 |
| WO | 2006008754 A1 | 1/2006 |

OTHER PUBLICATIONS

Becker D.P., et al., "A Short Synthesis of 1-Azaadamantan-4-One and the 4r and 4s Isomers of 4-Amino-1-Azaadamantane," Synthesis, 1992, vol. 11, pp. 1080-1082.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Eliel, E. L. et al., "Stereochemistry of Organic Compounds," 1994, John Wiley & Sons, Inc. New York. Table of Contents.
Fiedler., "Encyclopedia of Excipients for Pharmaceuticals, Cosmetics and related Areas," 5th Edition, Hoepfner E. M., et al., eds., Editio Cantor Verlag Aulendorf, 2002, Table of Contents.
Foster, A. B. et al., "Deuterium Isotope Effects in the Metabolism of Drugs and Xenobiotics: Implications for Drug Design," Advances in Drug Research, 1985, vol. 14, pp. 2-36.
Furniss B.S., et al., Vogel's Textbook of Practical Organic Chemistry, 5th Edition, Longman Scientific & Technical, 1989, Table of Contents.
Goodman, et al., The Pharmacological Basis of Therapeutics, 7th Edition, Macmillan Publishing Company, 1985, Table of Contents.
Greene T.W., et al., in: Protective Groups in Organic Synthesis, 3rd Edition, John Wiley and Sons, Inc., 1999, Preface, Table of Contents, Abbreviations.
Higuchi T., et al., eds., Pro-drugs as Novels Delivery Systems, vol. 14, ACS Symposium Series, 1975, Table of Contents.
Jones, C.D. et al., "Effects of Substituent Modification on Face Selection in Reduction," Journal of Organic Chemistry, 1998, vol. 63 (8), pp. 2758-2760.

(Continued)

*Primary Examiner* — Raymond Henley, III
(74) *Attorney, Agent, or Firm* — Lisa V. Mueller; Michael Best & Friedrich LLP

(57) ABSTRACT

An embodiment relates to a nicotinic acetylcholine receptor ligand, a therapeutically suitable salt, prodrug, or a metabolite thereof, for the prevention and treatment of diseases and conditions that are mediated by nicotinic acetylcholine receptors, and methods of use thereof. Another embodiment is a method of administering a pharmaceutically effective amount of a nicotinic acetylcholine receptor ligand, a therapeutically suitable salt, prodrug, or a metabolite thereof, to a mammal in need thereof.

8 Claims, 3 Drawing Sheets

(56) References Cited

OTHER PUBLICATIONS

Kato, S. et al., "Synthesis of Deuterated Mosapride Citrate," Journal of Labelled Compounds and Radiopharmaceuticals, 1995, vol. 36 (10), pp. 927-932.

Korolkovas A., "Development of Drugs" in: Essentials of Medicinal Chemistry, Second Edition, John Wiley and Sons, 1988, pp. 97-118.

Kushner, et al., "Pharmacological uses and perspectives of heavy water and deuterated compounds," Canadian Journal of Physiology and Pharmacology, 1999, vol. 77 (2), pp. 79-88.

Levin E.D., "Nicotinic Receptor Subtypes and Cognitive Function," Journal of Neurobiology, 2002, vol. 53 (4), pp. 633-640.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Mantripragada S., "A Lipid Based Depot (DepoFoam technology) for Sustained Release Drug Delivery," Progress in Lipid Research, 2002, vol. 41 (5), pp. 392-406.

Masters K., "Spray Drying Handbook" 4th Edition, John Wiley & Sons, 1985, Table of Contents.

Paterson D., et al., "Neuronal Nicotinic Receptors in the Human Brain," Progress in Neurobiology, 2000, vol. 61 (1), pp. 75-111.

Polymer Handbook, Brandrup J., et al., Eds., Interscience Publishers, 1975, Table of Contents, III-139-III-192.

Rochre E.B., ed., Bioreversible Carries in Drug Design Theory and Application, Pergamon Press, 1987, Table of Contents.

Sperling L. H., "Introduction to Physical Polymer Science," 2nd Edition, John Wiley & Sons, Inc., 1992, Table of Contents.

Thomson, J.F., "Physiological Effects of D20 in Mammals," Annals of the New York Academy of Sciences, 1960, vol. 84, pp. 736-744.

* cited by examiner

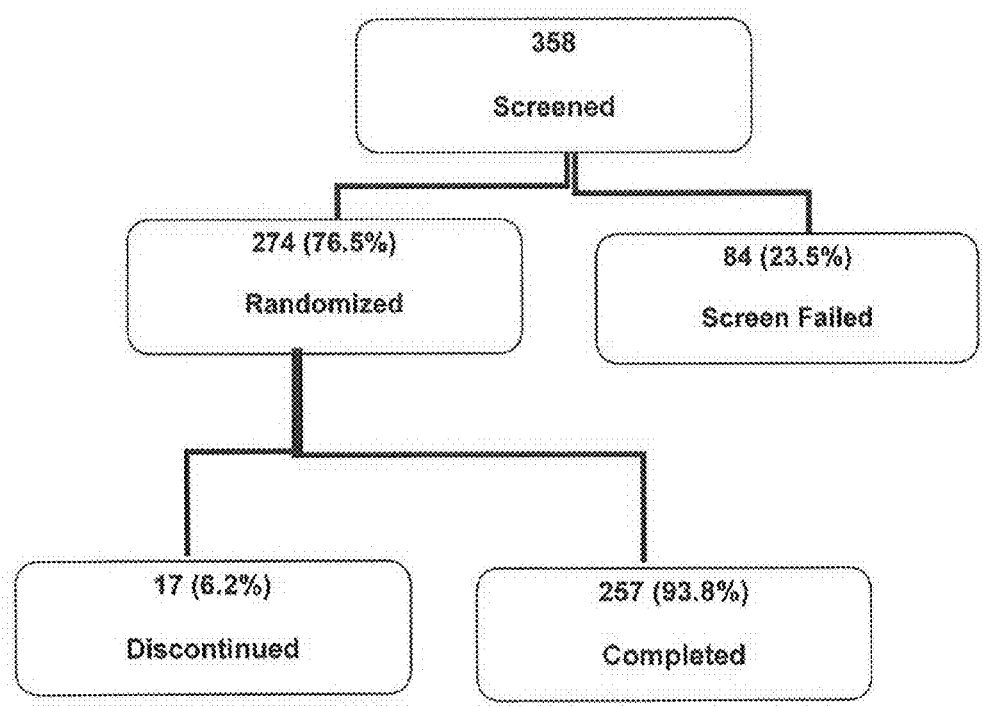

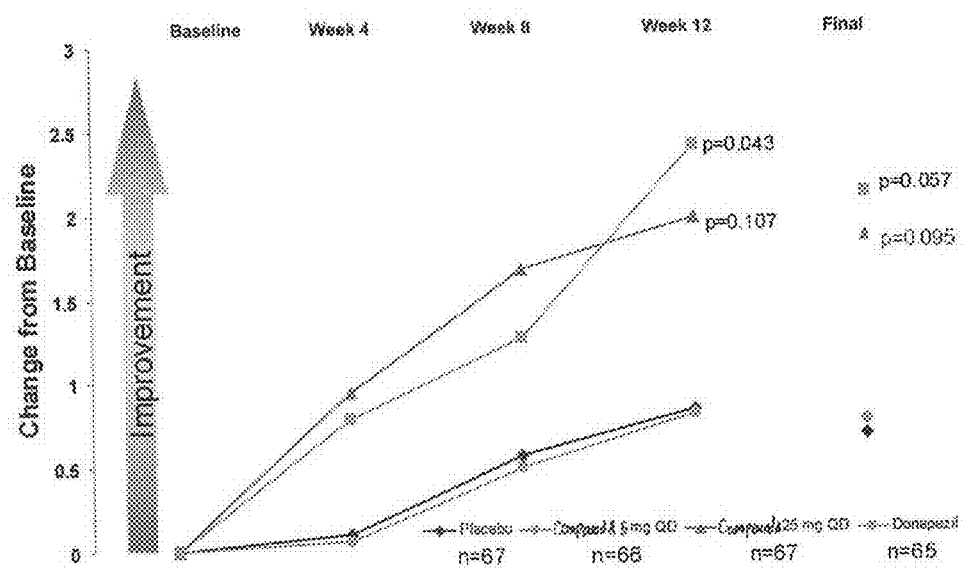

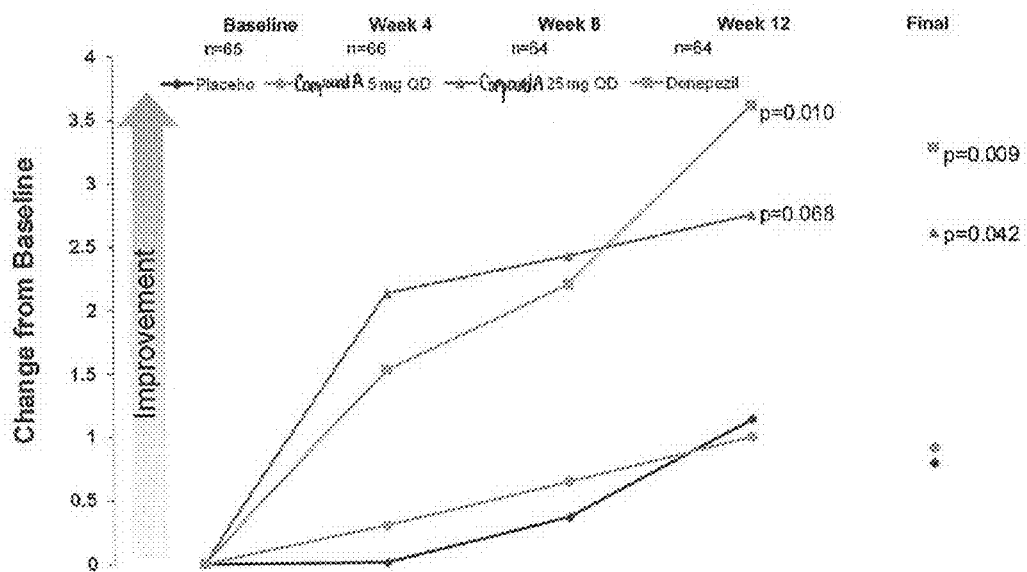

AZAADAMANTANE DERIVATIVES AND METHODS OF USE

CROSS-REFERENCE OF RELATED APPLICATIONS

This application claims priority from U.S. Provisional Patent Application Ser. No. 61/607,490, filed Mar. 6, 2012, U.S. Provisional Patent Application Ser. No. 61/594,262, filed Feb. 2, 2012, U.S. Provisional Patent Application Ser. No. 61/578,863, filed Dec. 21, 2011, U.S. Provisional Patent Application Ser. No. 61/545,943 filed Oct. 11, 2011, U.S. Provisional Patent Application Ser. No. 61/545,961, filed Oct. 11, 2011, and U.S. Provisional Patent Application Ser. No. 61/451,079, filed Mar. 9, 2011, each of which is hereby incorporated by reference in its entirety.

FIELD OF THE INVENTION

The present disclosure relates to compositions comprising ligands of α7-containing neuronal nicotinic acetylcholine receptors (nAChRs), α4β2 nAChRs, or both α7 and α4β2 nAChRs for the prevention and treatment of diseases and conditions that are mediated by selective interaction with α7-containing neuronal nAChRs, α4β2 nAChRs, or both α7 and α4β2 nAChRs, and methods of use thereof.

BACKGROUND OF THE INVENTION

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to, acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neurodegeneration, pain, inflammation, psychosis, sensory gating, mood, and emotion, among other conditions.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, α2-α10 and β2-β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition (α4)2(β2)3 (the α4β2 subtype), while another major population of receptors is comprised of homomeric (α7)5 (the α7 subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The α7 and α4β2 nAChRs have been shown to play a significant role in enhancing cognitive function, including aspects of learning, memory and attention (Levin, E. D., J. Neurobiol. 53: 633-640, 2002). For example, α7 nAChRs have been linked to conditions and disorders related to attention deficit disorder, attention deficit hyperactivity disorder (ADHD), schizophrenia, Alzheimer's disease (AD), mild cognitive impairment, senile dementia, dementia associated with Lewy bodies, dementia associated with Down's syndrome, AIDS dementia, and Pick's disease, as well as inflammation. The α4β2 receptor subtype is implicated in attention, cognition, epilepsy, and pain control (Paterson and Norberg, Progress in Neurobiology 61 75-111, 2000) as well as smoking cessation or nicotine withdrawal syndrome.

The activity at both α7 and α4β2 nAChRs can be modified or regulated by the administration of subtype selective nAChR ligands. The ligands can exhibit antagonist, agonist, or partial agonist properties. Compounds that function as allosteric modulators are also known.

Although compounds that nonselectively demonstrate activity at a range of nicotinic receptor subtypes including the α4β2 and α7 nAChRs are known, it would be beneficial to provide compounds that interact selectively with α7-containing neuronal nAChRs, α4β2 nAChRs, or both α7 and α4β2 nAChRs compared to other subtypes.

It would be beneficial to provide a nicotinic acetylcholine receptor ligand for treatment of nAChR-mediated conditions, for example disorders such as Alzheimer's disease, dementia, or other conditions related to a decline in cognitive function. There remains a need for providing a nicotinic acetylcholine receptor ligand that treats such conditions in a safe and efficacious manner.

SUMMARY OF THE INVENTION

It has been found that an α7 nicotinic acetylcholine receptor (nAChR) ligand, (4s)-4-(5-phenyl-1,3,4-thiadiazol-2-yloxy)-1-azatricyclo[3.3.1.1$^{3,7}$]decane, or salt thereof, is an effective compound for treatment of symptoms associated with Alzheimer's disease. Moreover, administration of (4s)-4-(5-phenyl-1,3,4-thiadiazol-2-yloxy)-1-azatricyclo [3.3.1.1$^{3,7}$]decane to human patients reduced the severity of symptoms associated with Alzheimer's disease in patients in a generally well tolerated manner. (4s)-4-(5-Phenyl-1,3,4-thiadiazol-2-yloxy)-1-azatricyclo [3.3.1.1$^{3,7}$]decane (ABT-126) demonstrated statistically significant efficacy compared to placebo in the treatment of the core symptoms of Alzheimer's disease in human patients.

BRIEF DESCRIPTION OF THE DRAWINGS

FIG. 1 graphically depicts the study disposition of subjects in an Alzheimer's Disease Phase 2a Proof-of-Concept Symptomatic Monotherapy Trial wherein (4s)-4-(5-phenyl-1,3,4-thiadiazol-2-yloxy)-1-azatricyclo[3.3.1.1$^{3,7}$]decane (hereinafter "Compound A") was administered.

FIG. 2 graphically depicts the mean change from baseline as measured by ADAS-Cog (11-item) of patients administered (4s)-4-(5-phenyl-1,3,4-thiadiazol-2-yloxy)-1-azatricyclo[3.3.1.1$^{3,7}$]decane in subjects with mild-to-moderate dementia of Alzheimer type in a Phase 2a clinical study when compared with placebo and donepezil, a commercially available active agent for Alzheimer's disease symptomatic treatment.

FIG. 3 graphically depicts the mean change from baseline as measured by ADAS-Cog (13-item) of patients administered (4s)-4-(5-phenyl-1,3,4-thiadiazol-2-yloxy)-1-azatricyclo[3.3.1.1$^{3,7}$]decane in subjects with mild-to-moderate dementia of Alzheimer type in a Phase 2a clinical study when compared with placebo and donepezil, a commercially available active agent for Alzheimer's disease symptomatic treatment.

DETAILED DESCRIPTION OF THE INVENTION

All patents, patent applications, and literature references cited in the specification are herein incorporated by reference in their entirety.

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used throughout this specification and the appended claims, the following terms have the following meanings
Definition of Terms As used throughout this specification and the appended claims, the following terms have the following meanings The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein.

Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio. The term "alkylthioalkyl" as used herein, means an alkylthio group, as defined herein, appended to the parent molecular moiety through an alkyl group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl. The term "alkynylene" means a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "alkynyloxy" as used herein, means an alkynyl group, as defined herein, appended to the parent molecular moiety through an oxygen atom. Representative examples of alkynyloxy include, but are not limited to, 2-propynyloxy and 2-butynyloxy.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, —NZ$_1$Z$_2$, and (NZ$_3$Z$_4$)carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "AUG$_\infty$" refers to the area under the plasma concentration time curve (AUC) extrapolated to infinity.

The term "azido" as used herein, means a —N$_3$ group.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$_1$Z$_2$, and (NZ$_3$Z$_4$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means cycloalkyl group, as defined herein, appended to the parent molecular moiety through a carbonyl group, as defined herein.

Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" as used herein, means —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothienyl(or benzothiophenyl), cinnolinyl, furopyridine, indolyl, indazolyl, indolinonyl, isobenzofuran, isoindolyl, isoquinolinyl, naphthyridinyl, oxadiazolyl, oxazolopyridine, quinolinyl, quinoxalinyl, thiadiazolyl, and thienopyridinyl.

The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$_1$Z$_2$ and (NZ$_3$Z$_4$)carbonyl. Heteroaryl groups of the invention that are substituted with a hydroxy group may be present as tautomers. The heteroaryl groups of the invention encompasses all tautomers including non-aromatic tautomers. In addition, the nitrogen heteroatoms can be optionally quaternized or oxidized to the N-oxide.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" as used herein, means a heteroarylalkyl, as defined herein, appended to the parent molecular moiety through a carbonyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio, and thien-3-ylmethylthio.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" as used herein, means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —NZ$_1$Z$_2$ and (NZ$_3$Z$_4$)carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkyl" as used herein, means a heterocycle, as defined herein, appended to the parent molecular moiety through an alkyl group, as defined herein. Representative examples of heterocyclealkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl.

The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-1-pyrrolidin-1-yl-butylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" as used herein, means a heterocyclealkyl group, as defined herein, appended to the parent molecular moiety through a sulfur atom. Representative examples of heterocyclealkylthio include, but are not limited to, 2-pyridin-3-ylethylthio, 3-quinolin-3-ylpropythio, and 5-pyridin-4-ylpentylthio.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" as used herein, means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxy groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower alkylthio" as used herein, is a subset of alkylthio, means a lower alkyl group, as defined herein, appended to the parent molecular moiety through a sulfur atom. Representative examples of lower alkylthio include, but are not limited to, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NZ$_1$Z$_2$" as used herein, means two groups, Z$_1$ and Z$_2$, which are appended to the parent molecular moiety through a nitrogen atom. Z$_1$ and Z$_2$ are each independently selected from the group consisting of hydrogen, alkyl, alkylcarbonyl, alkoxycarbonyl, aryl, arylalkyl, formyl and (NZ$_5$Z$_6$)carbonyl. In certain instances within the invention, Z$_1$ and Z$_2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. $Z_3$ and $Z_4$ are each independently selected from the group consisting of hydrogen, alkyl, aryl and arylalkyl. Representative examples of $NZ_3Z_4$ include, but are not limited to, amino, methylamino, phenylamino and benzylamino.

The term "$NZ_5Z_6$" as used herein, means two groups, $Z_5$ and $Z_6$, which are appended to the parent molecular moiety through a nitrogen atom. $Z_5$ and $Z_6$ are each independently selected from the group consisting of hydrogen, alkyl, aryl and arylalkyl. Representative examples of $NZ_5Z_6$ include, but are not limited to, amino, methylamino, phenylamino and benzylamino.

The term "($NZ_3Z_4$)carbonyl" as used herein, means a $NZ_3Z_4$ group, as defined herein, appended to the parent molecular moiety through a carbonyl group, as defined herein. Representative examples of ($NZ_3Z_4$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "tautomer" as used herein means a proton shift from one atom of a compound to another atom of the same compound wherein two or more structurally distinct compounds are in equilibrium with each other.

The term "therapeutically suitable excipient" refers to pharmaceutically suitable, solid, semi-solid or liquid fillers, diluents, encapsulating material, formulation auxiliary and the like. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents, and the like. Such therapeutic compositions may be administered parenterally, intracisternally, orally, rectally, intraperitoneally or by other dosage forms known in the art.

The term "therapeutically suitable metabolite" refers to a pharmaceutically active compound formed by the in vivo biotransformation of compounds of formula (I-V).

The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the compounds of formula (I-V) for example, by hydrolysis in blood.

The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups as defined herein. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The term "solid dispersion" refers to a system in a solid state (as opposed to a liquid or gaseous state) comprising at least two components, wherein one component is dispersed throughout the other component or components. For example, an active ingredient or a combination of active ingredients can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. These particles are often of less than 400 µm in size, such as less than 100, 10, or 1 µm in size. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

The terms "weight percent" or "percent by weight" or "% by weight" or "wt %" denote the weight of an individual component in a composition or mixture as a percentage of the weight of the composition or mixture.

Substituents attached to a cyclic moiety, for instance a cycloalkyl, aryl, or heterocycloalkyl moiety, can be represented as not bound to any particular atom, but rather as attached to bonds that perpendicularly intersect a side of the cyclic group. This notation is meant to indicate that the substituent can be bound to one of two or more atoms of the cyclic group.

Although typically it may be recognized that an asterisk is used to indicate that the exact subunit composition of a receptor is uncertain, for example a3b4* indicates a receptor that contains the a3 and b4 proteins in combination with other subunits, the term α7 as used herein is intended to include receptors wherein the exact subunit composition is both certain and uncertain. For example, as used herein α7 includes homomeric (α7)5 receptors and α7* receptors, which denote a nAChR containing at least one α7 subunit.

Compounds of the Invention

Compounds which may be used in the methods and compositions of the invention are those of the Formula (I),

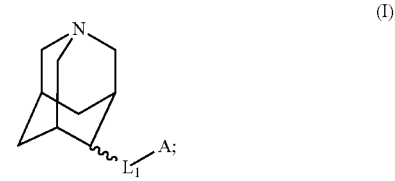

(I)

or a pharmaceutically acceptable salt or prodrug thereof, wherein $L_1$ is —O— or —$NR_a$—;

A is —$Ar_1$, —$Ar_2$-$L_2$-$Ar_3$ or —$Ar_4$-$L_3$-$Ar_5$;

$Ar_1$ is aryl or heteroaryl;

$Ar_2$ is aryl or monocyclic heteroaryl;

$Ar_3$ is aryl or heteroaryl;

$Ar_4$ is a bicyclic heteroaryl;

$Ar_5$ is aryl or heteroaryl;

$L_2$ is a bond, —O—, —$NR_a$—, —$CH_2$—, or —C(O)$NR_a$—;

$L_3$ is a bond, —O—, —$NR_a$— or —$CH_2$—; and $R_a$ is hydrogen or alkyl.

Another embodiment is a compound of formula (II),

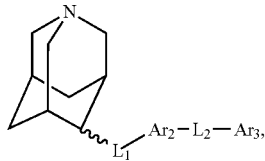

(II)

or a therapeutically suitable salt or prodrug thereof, wherein $Ar_2$ is selected from

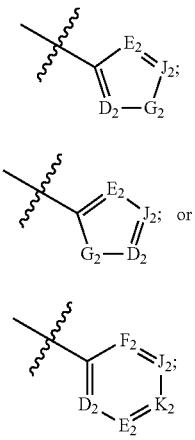

$D_2$, $E_2$, $F_2$, $J_2$, and $K_2$ are each independently —$CT_2$ or N;

$G_2$ is O, —$NR_{2a}$, or S;

in each group of (i), (ii), and (iii), one substituent represented by $T_2$, or $R_{2a}$ wherein $R_{2a}$ is $T_2$, is -$L_2$-$Ar_3$ and the other substituents represented by $T_2$ are hydrogen, alkyl, alkoxy, alkoxycarbonyl, cyano, halo, nitro, or —$NR_bR_c$;

$R_{2a}$ is hydrogen, alkyl, or $T_2$; and $R_b$ and $R_c$ are each independently hydrogen, alkyl, alkoxycarbonyl or alkylcarbonyl.

$Ar_3$ is a group selected from

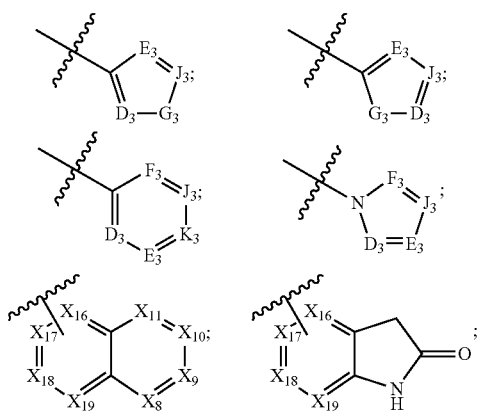

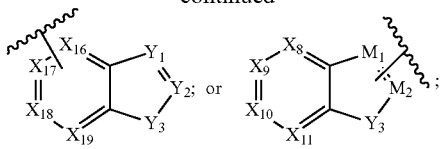

wherein $D_3$, $E_3$, $F_3$, $J_3$, $K_3$, $X_8$, $X_9$, $X_{10}$, and $X_{11}$ are each independently —$CR_3$ or N;

$X_{16}$, $X_{17}$, $X_{18}$, $X_{19}$, $M_1$, and $M_2$ are each independently —$CR_3$, N, or C;

$G_3$ is O, —$NR_{3a}$, or S;

$Y_1$ is —$CR_3$ or N;

$Y_2$ is —$CR_3$ or N;

$Y_3$ is NH, O, or S;

$R_3$ is hydrogen, alkyl, alkoxy, alkoxylalkyl, alkoxycarbonyl, alkylcarbonyl, cyano, halo, haloalkoxy, haloalkyl, hydroxy, nitro, $R_eR_fN$—, or aryl, wherein aryl is preferably phenyl optionally substituted with halo, alkyl or cyano;

$R_{3a}$ is hydrogen, alkyl, alkylcarbonyl, tritylaryl, wherein aryl is preferably phenyl;

$R_e$ and $R_f$ are each independently hydrogen, alkyl, alkoxycarbonyl, or alkylcarbonyl, or $R_e$ and $R_f$ are each taken together with the nitrogen atom to which they are attached form a heterocyclic ring, wherein the heterocyclic ring is preferably pyrrolidinyl, piperidinyl or piperazinyl;

one of $X_{16}$, $X_{17}$, $X_{18}$, and $X_{19}$, is C;

$M_1$ or $M_2$ is C;

$L_1$ is —O— or —$NR_a$—;

$L_2$ is a bond, —O—, —$NR_a$—, —$CH_2$—, or —C(O)$NR_a$—; and $R_a$ is hydrogen or alkyl.

Another embodiment is a compound of formula (III),

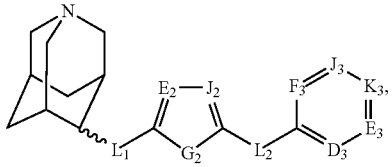

(III)

or a therapeutically suitable salt or prodrug thereof, wherein $E_2$ and $J_2$ are each independently —$CT_2$ or N;

$G_2$ is O, —$NR_{2a}$, or S;

$T_2$, at each occurrence, is independently hydrogen, alkyl, alkoxy, alkoxycarbonyl, cyano, halo, nitro, or —$NR_bR_c$;

$R_{2a}$ is hydrogen, alkyl, or $T_2$;

$R_b$ and $R_c$ are each independently hydrogen, alkyl, alkoxycarbonyl or alkylcarbonyl;

$D_3$, $E_3$, $F_3$, $J_3$, and $K_3$ are each independently —$CR_3$ or N;

$R_3$ is hydrogen, alkyl, alkoxy, alkoxylalkyl, alkoxycarbonyl, alkylcarbonyl, cyano, halo, haloalkoxy, haloalkyl, hydroxy, nitro, $R_eR_fN$—, or aryl, wherein aryl is preferably phenyl optionally substituted with halo, alkyl or cyano;

$R_e$ and $R_f$ are each independently hydrogen, alkyl, alkoxycarbonyl, or alkylcarbonyl, or $R_e$ and $R_f$ are each taken together with the nitrogen atom to which they are attached form a heterocyclic ring, wherein the heterocyclic ring is preferably pyrrolidinyl, piperidinyl or piperazinyl;

$L_1$ is —O— or —$NR_a$—;

$L_2$ is a bond, —O—, —$NR_a$—, —$CH_2$—, or —C(O)$NR_a$—; and $R_a$ is hydrogen or alkyl.

Another embodiment is a compound of formula (IV),

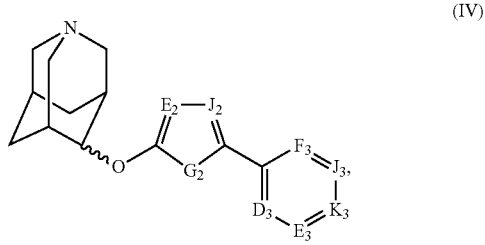

(IV)

or a therapeutically suitable salt or prodrug thereof, wherein $E_2$ and $J_2$ are each independently —$CT_2$ or N;

$G_2$ is O, —$NR_{2a}$, or S;

$T_2$, at each occurrence, is independently hydrogen, alkyl, alkoxy, alkoxycarbonyl, cyano, halo, nitro, or —$NR_bR_c$;

$R_{2a}$ is hydrogen, alkyl, or $T_2$;

$R_b$ and $R_c$ are each independently hydrogen, alkyl, alkoxycarbonyl or alkylcarbonyl;

$D_3$, $E_3$, $F_3$, $J_3$, and $K_3$ are each independently —$CR_3$ or N;

$R_3$ is hydrogen, alkyl, alkoxy, alkoxylalkyl, alkoxycarbonyl, alkylcarbonyl, cyano, halo, haloalkoxy, haloalkyl, hydroxy, nitro, $R_eR_fN$—, or aryl, wherein aryl is preferably phenyl optionally substituted with halo, alkyl or cyano; and $R_e$ and $R_f$ are each independently hydrogen, alkyl, alkoxycarbonyl, or alkylcarbonyl, or $R_e$ and $R_f$ are each taken together with the nitrogen atom to which they are attached form a heterocyclic ring, wherein the heterocyclic ring is preferably pyrrolidinyl, piperidinyl or piperazinyl.

Another embodiment is a compound of formula (V),

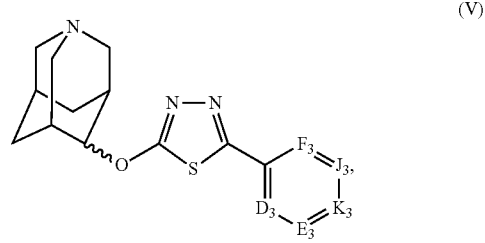

(V)

or a therapeutically suitable salt or prodrug thereof, wherein $D_3$, $E_3$, $F_3$, $J_3$, and $K_3$ are each independently —$CR_3$ or N;

$R_3$ is hydrogen, alkyl, alkoxy, alkoxylalkyl, alkoxycarbonyl, alkylcarbonyl, cyano, halo, haloalkoxy, haloalkyl, hydroxy, nitro, $R_eR_fN$—, or aryl, wherein aryl is preferably phenyl optionally substituted with halo, alkyl or cyano; and $R_e$ and $R_f$ are each independently hydrogen, alkyl, alkoxycarbonyl, or alkylcarbonyl, or $R_e$ and $R_f$ are each taken together with the nitrogen atom to which they are attached form a heterocyclic ring, wherein the heterocyclic ring is preferably pyrrolidinyl, piperidinyl or piperazinyl.

Another embodiment is (4s)-4-(5-phenyl-1,3,4-thiadiazol-2-yloxy)-1-azatricyclo[3.3.1.1$^{3,7}$]decane (Compound A).

The preparation of compounds of the invention is disclosed in US Patent Application Publication No. 20080167336.

Another compound which may be used for the methods and compositions of the invention is TC-5619, an α7 neuronal nicotinic receptor.

Another compound which may be used for the methods and compositions of the invention is EVP-6124, an α7 neuronal nicotinic receptor.

Salts of the Invention

The present compounds may exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts may be prepared during the final isolation and purification of the compounds or separately by reacting an amino group of the compounds with a suitable acid. For example, a compound may be dissolved in a suitable solvent, such as but not limited to methanol and water, and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides, and iodides such as methyl, ethyl, propyl, isopropyl, butyl, lauryl, myristyl, stearyl, and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

Amides, Esters and Prodrugs of the Invention

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

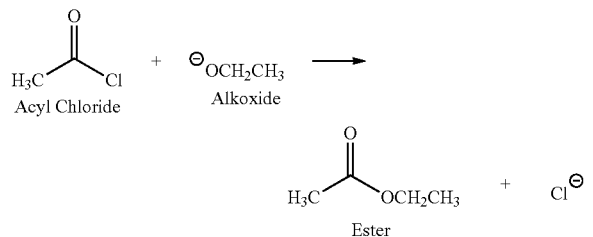

Amides can be prepared from substrates of formula (I) containing either an amino group or a carboxy group in similar fashion. Esters can also react with amines or ammonia to form amides.

Scheme 2

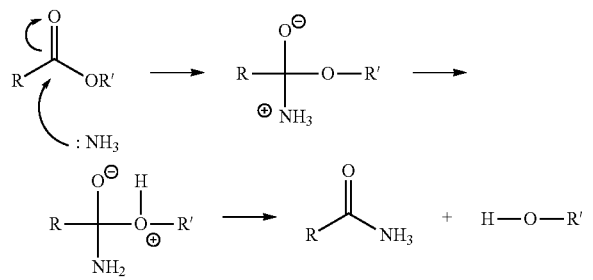

Another way to make amides from compounds of formula (I) is to heat carboxylic acids and amines together.

Scheme 3

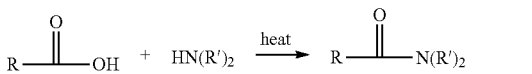

In Schemes 2 and 3, R and R' are independently substrates of formulas I-V, alkyl or hydrogen.

Optical Isomers-Diastereomers-Geometric Isomers

Asymmetric centers may exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well known in the art.

Geometric isomers may exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 63: 2758-2760, 1998.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

More particularly, the compounds of the invention can exist in the forms represented by formula (Ia) and (Ib).

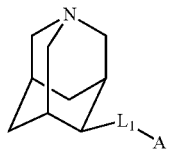
(1a)

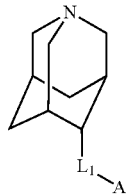
(1b)

The aza-adamantane portion of isomer (Ia) and isomer (Ib) is not chiral, however the C-4 carbon at which $L_1$ is attached is considered pseudoasymmetric. Compounds represented by formula (Ia) and (Ib) are diastereomers. The configurational assignment of structures of formula (Ia) are assigned 4r in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Ib) are assigned 4s using the same methods.

The isomers (Ia) and (Ib) may be synthesized separately using the individual steroisomers according to the Schemes or the Experimentals described herein. Alternatively, isomers (Ia) and (Ib) may be synthesized together after which the individual isomers may be separated by chromatographic methods from the mixture of both isomers when mixtures of stereoisomers are used in the synthesis. The mixtures of isomers may also be separated through fractional crystallization of salts of amines contained in the compounds of formula (I) made with enantiomerically pure carboxylic acids.

It is contemplated that a mixture of both isomers may be used to modulate the effects of nAChRs. Furthermore, it is contemplated that the individual isomers of formula (Ia) and (Ib) may be used alone to modulate the effects of nAChRs. Therefore, it is contemplated that either a mixture of the compounds of formula (Ia) and (Ib) or the individual isomers alone represented by the compounds of formula (Ia) or (Ib) would be effective in modulating the effects of nAChRs, and more particularly α7 nAChRs, α4β2 nAChRs, or a combination of α7 nAChRs and α4β2 nAChRs and is thus within the scope of the invention.

More specifically, compounds contemplated as part of the invention include

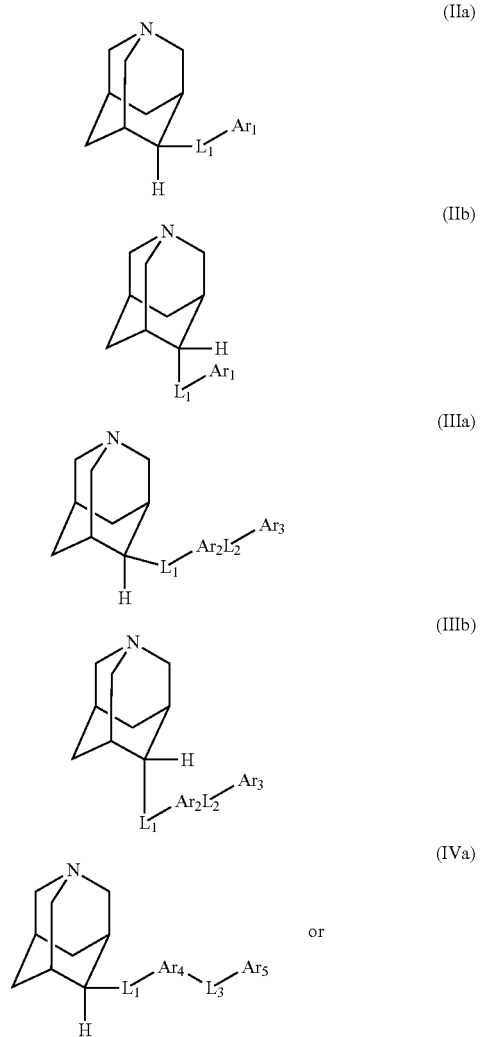

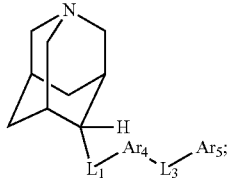

wherein $L_1$, $L_2$, $L_3$, $Ar_1$, $Ar_2$, $Ar_3$, $Ar_4$, and $Ar_5$ are defined herein.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of nAChR ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to nAChR activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Stable isotope labeling of a drug can alter its physico-chemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-istopic compound.

Compositions of the Invention

Therapeutic compositions of the disclosure comprise an effective amount of an nAChR ligands of formulas I-V, or pharmaceutically acceptable salts, prodrugs, esters, amides or metabolites thereof formulated with one or more therapeutically suitable excipients.

In one embodiment, the therapeutically effective amount comprises an amount of the nAChR ligand from about 0.01 mg to about 250 mg. In another embodiment the therapeutically effective amount is selected from the group consisting of about 0.01 mg to about 250 mg, about 0.01 mg to about 225 mg, about 0.01 mg to about 200 mg, 0.01 mg to about 175 mg, about 0.01 mg to about 150 mg, about 0.01 mg to about 125 mg, about 0.01 mg to about 100 mg, about 0.01 mg to about 75 mg, about 0.01 mg to about 50 mg, about 0.01 mg to about 25 mg, about 0.01 mg to about 20 mg, about 0.01 mg to about 15 mg, about 0.01 mg to about 10 mg, about 0.01 mg to about 5 mg, about 0.01 mg to about 4 mg, about 0.01 mg to about 3 mg, about 0.01 mg to about 2 mg, about 0.01 mg to about 1 mg, about 0.01 mg to about 0.1 mg, about 0.1 mg to about 1 mg, about 0.1 mg to about 0.5 mg, and about 0.1 mg to about 0.2 mg.

In another embodiment, the therapeutically effective amount of Compound A comprises an amount of the nAChR ligand from about 0.01 mg to about 250 mg. In another embodiment the therapeutically effective amount is selected from the group consisting of about 0.01 mg to about 250 mg, about 0.01 mg to about 225 mg, about 0.01 mg to about 200 mg, 0.01 mg to about 175 mg, about 0.01 mg to about 150 mg, about 0.01 mg to about 125 mg, about 0.01 mg to about 100 mg, about 0.01 mg to about 75 mg, about 0.01 mg to about 50 mg, about 0.01 mg to about 25 mg, about 0.01 mg to about 20 mg, about 0.01 mg to about 15 mg, about 0.01 mg to about 10 mg, about 0.01 mg to about 5 mg, about 0.01 mg to about 4 mg, about 0.01 mg to about 3 mg, about 0.01 mg to about 2 mg, about 0.01 mg to about 1 mg, about 0.01 mg to about 0.1 mg, about 0.1 mg to about 1 mg, about 0.1 mg to about 0.5 mg, and about 0.1 mg to about 0.2 mg.

In another embodiment, the therapeutically effective amount of Compound A comprises an amount of the nAChR ligand from about 25 mg to about 75 mg. Compound A is administered in doses of 25 mg, 50 mg, or 75 mg.

Liquid dosage forms for oral administration include, but are not limited to, emulsions, microemulsions, solutions, suspensions, syrups, and elixirs. Liquid dosage forms may also contain diluents, solubilizing agents, emulsifying agents, inert diluents, wetting agents, emulsifiers, sweeteners, flavorants, perfuming agents and the like.

Injectable preparations include, but are not limited to, sterile, injectable, aqueous, oleaginous solutions, suspensions, emulsions and the like. Such preparations may also be formulated to include, but are not limited to, parenterally suitable diluents, dispersing agents, wetting agents, suspending agents and the like. Such injectable preparations may be sterilized by filtration through a bacterial-retaining filter. Such preparations may also be formulated with sterilizing agents that dissolve or disperse in the injectable media or other methods known in the art.

The absorption of the compounds of the present invention may be delayed using a liquid suspension of crystalline or amorphous material having poor water solubility. The rate of absorption of the compounds generally depends upon the rate of dissolution and crystallinity. Delayed absorption of a parenterally administered compound may also be accomplished by dissolving or suspending the compound in oil. Injectable depot dosage forms may also be prepared by microencapsulating the same in biodegradable polymers. The rate of drug release may also be controlled by adjusting the ratio of compound to polymer and the nature of the polymer employed. Depot injectable formulations may also prepared by encapsulating the compounds in liposomes or microemulsions compatible with body tissues.

Solid dosage forms for oral administration include, but are not limited to, capsules, tablets, gels, pills, powders, granules and the like. The drug compound is generally combined with at least one therapeutically suitable excipient, such as carriers, fillers, extenders, disintegrating agents, solution retarding agents, wetting agents, absorbents, lubricants and the like. Capsules, tablets, and pills may also contain buffering agents. Suppositories for rectal administration may be prepared by mixing the compounds with a suitable non-irritating excipient that is solid at ordinary temperature but fluid in the rectum.

The present drug compounds may also be microencapsulated with one or more excipients. Tablets, dragees, capsules, pills, and granules may also be prepared using coatings and shells, such as enteric and release or rate controlling polymeric and nonpolymeric materials. For example, the compounds may be mixed with one or more inert diluents. Tableting may further include lubricants and other processing aids. Similarly, capsules may contain opacifying agents that delay release of the compounds in the intestinal tract.

A transdermal patch or skin patch is a medicated adhesive patch that is placed on the skin to deliver a specific dose of medication through the skin into the bloodstream. Transdermal patches have the added advantage of providing controlled delivery of the present compounds to the body. Such dosage forms are prepared by dissolving or dispensing the compounds in suitable medium. Absorption enhancers may also be used to increase the flux of the compounds across the skin.

The rate of absorption may be controlled by employing a rate controlling membrane. The compounds may also be incorporated into a polymer matrix or gel.

For a given dosage form, disorders of the present invention may be treated, prophylatically treated, or have their onset delayed in a patient by administering to the patient a therapeutically effective amount of compound of the present invention in accordance with a suitable dosing regimen. In other words, a therapeutically effective amount of any one of compounds of formulas I thru V is administered to a patient to treat and/or prophylatically treat disorders modulated by nicotinic acetylcholine receptors. The specific therapeutically effective dose level for a given patient population may depend upon a variety of factors including, but not limited to, the specific disorder being treated, the severity of the disorder; the activity of the compound, the specific composition or dosage form, age, body weight, general health, sex, diet of the patient, the time of administration, route of administration, rate of excretion, duration of the treatment, drugs used in combination, coincidental therapy and other factors known in the art.

The present disclosure also includes therapeutically suitable metabolites formed by in vivo biotransformation of any of the compounds of formulas I-V. Pharmaceutically active metabolites include, but are not limited to, compounds made by adamantane hydroxylation or polyhydroxylation of any of the compounds of formulas (I-V). A discussion of biotransformation is found in Goodman and Gilman's, The Pharmacological Basis of Therapeutics, seventh edition, MacMillan Publishing Company, New York, N.Y., (1985).

Solid Compositions

The present disclosure features solid compositions comprising a nAChR ligand of formulas I-V, or pharmaceutically acceptable salts, prodrugs, esters, amides or metabolites thereof.

An embodiment is a solid compositions comprising a nAChR ligand of formulas I-V, or pharmaceutically acceptable salts, prodrugs, esters, amides or metabolites thereof, a pharmaceutically acceptable hydrophilic polymer, and a pharmaceutically acceptable surfactant.

A non-limiting way to form an amorphous form of the nAChR ligand is through the formation of solid dispersions with a polymeric carrier. The presence of hydrophilic polymer(s) and surfactant(s), as well as the dispersion of Compound A in an amorphous form in a matrix containing the polymer(s), can significantly enhance the dissolution rate of Compound A. In some cases, a solid dispersion formulation can also effectively maintain Compound A in its supersaturation state to allow for better absorption.

In one aspect, the present invention features a solid composition comprising the nAChR ligand in an amorphous form, a pharmaceutically acceptable hydrophilic polymer, and a pharmaceutically acceptable surfactant. The nAChR ligand and the polymer are formulated in a solid dispersion. The surfactant may also be formulated in the same solid dispersion; or the surfactant can be separately combined or mixed with the solid dispersion.

In one embodiment, a solid composition of the invention comprises an amorphous solid dispersion which comprises the nAChR ligand, a pharmaceutically acceptable hydrophilic polymer and a pharmaceutically acceptable surfactant. In another embodiment, a solid composition of the invention comprises a solid solution which comprises the nAChR ligand and a pharmaceutically acceptable hydrophilic polymer. In still another embodiment, a solid composition of the invention comprises a solid solution which comprises the nAChR ligand, a pharmaceutically acceptable hydrophilic polymer and a pharmaceutically acceptable surfactant. In yet another embodiment, a solid composition of the invention comprises a glassy solution which includes the nAChR ligand and a pharmaceutically acceptable hydrophilic polymer. In a further embodiment, a solid composition of the invention comprises a glassy solution which includes the nAChR ligand, a pharmaceutically acceptable hydrophilic polymer and a pharmaceutically acceptable surfactant. A solid composition of the invention can contain, for example, from 1 to 50% by weight of the nAChR ligand. For instance, a solid composition of the invention can contain from 5 to 30% by weight of the nAChR ligand. Preferably, a solid composition of the invention contains from 5 to 15% by weight of the nAChR ligand.

A solid dispersion of the invention may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion of the invention may also contain at least 1% by weight of a pharmaceutically acceptable surfactant or a combination of such surfactants. Preferably, the solid dispersion contains at least 2% by weight of a pharmaceutically acceptable surfactant or a combination of such surfactants. More preferably, the solid dispersion contains from about 4% to about 20% by weight of the surfactant(s), such as from about 5% to about 10% by weight of the surfactant(s).

In one embodiment, a solid dispersion of the invention comprises at least 30% by weight of a pharmaceutically acceptable hydrophilic polymer or a combination of such polymers, and at least 1% by weight of a pharmaceutically acceptable surfactant or a combination of such surfactants. In another embodiment, a solid dispersion of the invention comprises at least 50% by weight of a pharmaceutically acceptable hydrophilic polymer or a combination of such polymers, and from about 2% to about 20% by weight of a pharmaceutically acceptable surfactant or a combination of such surfactants. In yet another embodiment, a solid dispersion of the invention comprises from about 50% to about 90% by weight of a pharmaceutically acceptable hydrophilic polymer or a combination of such polymers, and from about 3% to about 15% by weight of a pharmaceutically acceptable surfactant or a combination of such surfactants. In yet another embodiment, a solid dispersion of the invention comprises from about 70% to about 90% by weight of a pharmaceutically acceptable hydrophilic polymer or a combination of such polymers, and from about 5% to about 10% by weight of a pharmaceutically acceptable surfactant or a combination of such surfactants.

In one embodiment, the hydrophilic polymer employed in the present invention has a $T_g$ of at least 50° C., more preferably at least 60° C., and highly preferably at least 80° C. including, but not limited to, from about 80° C. to about 180° C., or from about 100° C. to about 150° C. Methods for determining $T_g$ values of organic polymers are described in INTRODUCTION TO PHYSICAL POLYMER SCIENCE (2nd Edition by L. H. Sperling, published by John Wiley & Sons, Inc., 1992). The $T_g$ value can be calculated as the weighted sum of the $T_g$ values for homopolymers derived from each of the individual monomers, i.e., the polymer $T_g = \Sigma W_i \cdot X_i$ where $W_i$ is the weight percent of monomer i in the organic polymer, and $X_i$ is the $T_g$ value for the homopolymer derived from monomer i.

$T_g$ values for the homopolymers may be taken from POLYMER HANDBOOK (2nd Edition by J. Brandrup and E. H. Immergut, Editors, published by John Wiley & Sons, Inc., 1975). Hydrophilic polymers with a $T_g$ as described above may allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids. Hydrophilic polymers having a $T_g$ of below 50° C. may also be used.

In another embodiment, the solid dispersion comprises a water-soluble hydrophilic polymer. A solid composition of the present invention can also comprise poorly water-soluble or water-insoluble polymer or polymers, such as cross-linked polymers. A hydrophilic polymer comprised in a solid composition of the present invention preferably has an apparent viscosity, when dissolved at 20° C. in an aqueous solution at 2% (w/v), of 1 to 5000 mPa·s., and more preferably of 1 to 700 mPa·s, and most preferably of 5 to 100 mPa·s.

Hydrophilic polymers suitable for use in a solid composition of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); or any mixture thereof.

Non-limiting examples of preferred hydrophilic polymers for the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in the present invention is preferably a non-ionic surfactant. More preferably, a solid composition of the present invention comprises a pharmaceutically acceptable surfactant having an HLB value of from about 2 to about 20. A solid composition of the present invention can also include a mixture of pharmaceutically acceptable surfactants, with at least one surfactant having an HLB value of no less than 10 and at least another surfactant having an HLB value of below 10. In one example, each surfactant comprised in a solid composition of the invention has an HLB value of at least 10. In another example, each surfactant comprised in a solid composition of the invention has an HLB value of below 10. In yet another example, a solid composition of the present invention includes at least two pharmaceutically acceptable surfactants, one having an HLB value of at least 10 and the other having an HLB value of below 10. The HLB system (Fiedler, H. B., ENCYLOPEDIA OF EXCIPIENTS, 5th ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for the present invention include polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60); or a mono fatty acid ester of polyoxyethylene sorbitan, such as a mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate, sucrose dilaurate; sorbitan fatty acid mono esters such as sorbitan mono laurate (Span® 20), sorbitan monooleate, sorbitan monopalnitate (Span® 40), or sorbitan stearate. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, or Poloxamer® 407 (BASF Wyandotte Corp.). As described above, a mixture of surfactants can be used in a solid composition of the present invention.

Non-limiting examples of preferred surfactants for the invention include to polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, and sorbitan monolaurate.

In one embodiment, a solid composition of the present invention comprises an amorphous solid dispersion or a solid solution which includes Compound A (or a pharmaceutically acceptable salt thereof) and a pharmaceutically acceptable hydrophilic polymer. The solid composition also includes a pharmaceutically acceptable surfactant which preferably is formulated in the amorphous solid dispersion or solid solution. The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor® EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor® RH 40, also known as polyoxyl 40 hydrogenated castor oil or macrogolglycerol hydroxystearate), polyethylenglycol 60 hydrogenated castor oil (Cremophor® RH 60), a mono fatty acid ester of polyoxyethylene (20) sorbitan (e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, sucrose monostearate, sucrose distearate, sucrose monolaurate, sucrose dilaurate, sorbitan monolaurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from sorbitan monolaurate or D-alpha-tocopheryl polyethylene glycol 1000 succinate.

In another embodiment, a solid composition of the present invention comprises an amorphous solid dispersion or solid solution which includes Compound A (or a pharmaceutically acceptable salt thereof) and a homopolymer or copolymer of N-vinyl pyrrolidone (e.g., copovidone). The solid composition also comprises a pharmaceutically acceptable surfactant (e.g., vitamin E TPGS, or sorbitan monolaurate), wherein the surfactant preferably is formulated in the amorphous solid dispersion or solid solution.

In yet another embodiment, a solid composition of the present invention comprises an amorphous solid dispersion or solid solution which includes Compound A (or a pharmaceutically acceptable salt thereof), copovidone, and a pharmaceutically acceptable surfactant selected from vitamin E TPGS or sorbitan monolaurate. The amorphous solid dispersion or solid solution may also include another pharmaceutically acceptable surfactant.

A solid dispersion employed in the present invention preferably comprises or consists of a single-phase (defined in thermodynamics) in which the therapeutic agent (e.g., Compound A) and the pharmaceutically acceptable hydrophilic polymer are molecularly dispersed. In such cases, thermal analysis of the solid dispersion using differential scanning calorimetry (DSC) typically shows only one single $T_g$, and the solid dispersion does not contain any detectable crystalline ligand as measured by X-ray powder diffraction spectroscopy.

In another embodiment, the solid composition is a solid oral dosage form. Common solid oral dosage forms suitable for the present invention include, but are not limited to, capsules, dragees, granules, pills, powders and tablets, with capsules and tablets being preferred. A solid oral dosage form of the present invention can also include other excipients or inset diluents, such as microcrystalline cellulose, dibasic calcium phosphate, starch, mannitol, sucrose or lactose. Lubricants, glidants, binders, coloring agents, releasing agents, coating agents, sweetening or flavoring agents, buffering agents, preservatives, or antioxidants can also be included in a solid oral dosage form of the present invention.

A solid dosage form of the present invention can be prepared by conventional techniques such as blending, screening, lubrication and encapsulation into hard gelatin capsules or compression into tablets. It could also be made by granulation using wet or dry processes, drying, screening, lubrication and encapsulation or tablet compression.

A solid composition of the present invention can be prepared by a variety of techniques such as, without limitation, melt-extrusion, spray-drying, co-precipitation, freeze drying, or other solvent evaporation techniques. The melt-extrusion process typically comprises the steps of preparing a melt which includes the active ingredient(s), the hydrophilic polymer(s) and preferably the surfactant(s), and then cooling the melt until it solidifies. "Melting" means a transition into a liquid or rubbery state in which it is possible for one component to get embedded, preferably homogeneously embedded, in the other component or components. In many cases, the polymer component(s) will melt and the other components including the active ingredient(s) and surfactant(s) will dissolve in the melt thereby forming a solution. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the surfactant(s) is molten externally and pumped in during extrusion.

In another example, the melt comprises the nAChR ligand and one or more hydrophilic polymers described above, and the melt temperature is in the range of from about 100 to about 170° C., from about 120 to about 150° C., and from about 135 to about 140° C. The melt can also include a pharmaceutically acceptable surfactant described above.

To start a melt-extrusion process, the active ingredient(s) (e.g., the nAChR ligand) can be employed in their solid forms, such as their respective crystalline forms. The active ingredient(s) can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multiscrew extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of the active ingredient(s) in a matrix comprised of the hydrophilic polymer(s) and optionally the pharmaceutically acceptable surfactant(s). Where the granules do not contain any surfactant, a pharmaceutically acceptable surfactant described above can be added to and blended with the granules. The extrusion product can also be blended with other active ingredient(s) and/or additive(s) before being milled or ground to granules. The granules can be further processed into suitable solid oral dosage forms.

In one example, copovidone and one or more surfactants are mixed and granulated, followed by the addition of aerosil and the nAChR ligand. The mixture, which may contain for example 5% by weight of the nAChR ligand, is then milled. The mixture is then subject to extrusion, and the extrudate thus produced can be milled and sieved for further processing to make capsules or tablets. Surfactant(s) employed in this example can also be added through liquid dosing during extrusion.

The approach of solvent evaporation, via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet and/or co-formulation with the nAChR ligand is desired.

Exemplary spray-drying processes and spray-drying equipment are described in K. Masters, SPRAY DRYING HANDBOOK (Halstead Press, New York, 4th ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means.

The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of the active ingredient(s) in a matrix comprised of the hydrophilic polymer(s) and optionally the pharmaceutically acceptable surfactant(s). Where the spray dried product does not contain any surfactant, a pharmaceutically acceptable surfactant described above can be added to and blended with the spray-dried product before further processing.

Before feeding into a spray dryer, the active ingredient(s) (e.g., the nAChR ligand), the hydrophilic polymer(s), as well as other optional active ingredients or excipients such as the pharmaceutically acceptable surfactant(s), can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches.

At least one additive selected from flow regulators, binders, lubricants, fillers, disintegrants, or plasticizers may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from about 1000 to about 6000), magnesium and calcium stearates, sodium stearyl fumarate, and the like.

Various other additives may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack. Solid compositions according to certain embodiments of the present invention may contain several layers, for example laminated or multilayer tablets. They can be in open or closed form. "Closed dosage forms" are those in which one layer is completely surrounded by at least one other layer.

In order to facilitate the intake of a solid dosage form, it is advantageous to give the dosage form an appropriate shape. Large tablets that can be swallowed comfortably are therefore preferably elongated rather than round in shape. A film coat on the tablet further contributes to the ease with which it can be swallowed. A film coat also improves taste and provides an elegant appearance. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. In one embodiment, the film coat may account for less than 5% by weight of a pharmaceutical composition of the present invention.

In another aspect, the present invention feature methods of using solid compositions of the present invention to treat diseases and disorders mediated by nicotinic acetylcholine receptors. The methods comprise administering a solid composition of the present invention to a patient in need thereof. The specific dose for any particular patient will depend upon a variety of factors such as the specific solid composition employed; the age, body weight, general health, sex and diet of the patient; the time of administration and rate of excretion; the duration of the treatment; drugs used in combination or coincidental with the nAChR ligand; and like factors well known in the medical arts.

A summary of technologies and experimental plans that can be used to achieve the targeted doses is listed in the summary below.

Summary of Technologies and Potential features
Parenteral
Drug Alone—Oily Suspension When using the Compound A alone, a suspension can be prepared in a vegetable oil. A prodrug with the desirable physicochemical properties can also be used for preparing a parenteral controlled release product.

The release of a drug in a suspension is mainly governed by the dissolution rate of the drug. A suspension can be injected either IM or SC for sustained systemic or local effects. The bioavailability of a prodrug is controlled by its bioconversion rate and a prodrug product can be administered IV or IM/SC depending on whether the final product is a solution or a dispersion system.

Dosage: 0.01-100 mg, once/week or once/3 days.

Drug—w/Carrier

Lipid emulsions: Compound A can be contained in the aqueous phase of a w/o system. The release of a drug from the internal phase is mainly achieved by partition and diffusion, and the drug can be administered through IV (for submicron emulsions only), SC or IM for systemic or local effect.

Dosage: 0.01-100 mg, SC or IM injection, Once/week or Once/3 days.

Lipid microspheres: Compound A particles are embedded in the matrix of solid lipid microparticles. The drug containing lipid micropheres can be formulated either as a ready-to-use dispersion or a powder for reconstitution for SC or IM injection. Drug release from lipid microspheres is controlled by drug diffusion and lipid degradation (see FIG. 7).

Dosage: 0.01-100 mg, SC or IM injection, Once/week or Once/3 days.

Liposomes: Liposomes are microscopic spherical vesicles consisting of amphiphilic phospholipid molecules which form bilayer membranes surrounding an aqueous core. Compound A can be encapsulated within the aqueous core or associated with the bilayer membrane. The release of drug is controlled by diffusion and direct cellular uptake (membrane fusion/endocytosis). When a liposome is coupled with a ligand specific to tumor cells, it can deliver the drug targeting at the tumor site Liposomes can either be injected through IV or IM/SC.

Dosage: 0.01-100 mg, SC or IM injection, Once/week or Once/3 days.

Lipid Based Depot: DepoFoams® are spherical lipid vesicles consisting of numerous small water filled compartments surrounded by phospholipid bilayers. Compound A can be entrapped in these compartments and their release is achieved by diffusion through the phospholipid bilayers which undergo phase transition at body temperature. Depo-Foam-encapsulation has been shown to result in sustained-release lasting over several days to weeks after non-vascular administration. The routes of administration most viable for delivery of drugs via DepoFoam formulations include intrathecal, epidural, subcutaneous, intramuscular, intra-atricular, and intraocular. DepoFoam particles are distinguished structurally from unilamellar vesicles, multilamellar vesicles, and neosomes in that each particle comprises a set of closely packed non-concentric vesicles. The particles are tens of microns in diameter and have large trapped volume, thereby affording delivery of large quantities of drugs in the encapsulated form in a small volume of injection. A number of methods based on a manipulation of the lipid and aqueous composition can be used to control the rate of sustained-release from a few days to several weeks (Mantripragada, Prog Lipid Res., 41(5):392-406 (2002).

Dosage: 0.01-100 mg, SC or IM injections, Once/week or Once/3 days.

Implants, Polymeric Systems

Biodegradable polymers decompose to form nontoxic components in vivo, thereby no post-treatment removal of the polymers is necessary. PLGA copolymers are the most widely used biodegradable polymers for parenteral products. Other polymers that have been used for parenteral products are polyanhydrides, polyphosphoesters, and polyorthoesters. Microspheres and in vivo gelling liquids are the two major types of parenteral controlled release products prepared using biodegradable polymers.

Dosage: 0.01-100 mg.

Polymeric Microspheres Implants

In polymeric microspheres, depending on the method of fabrication, Compound A can be encapsulated in the core or the matrix of the microspheres. Microspheres containing the drug are usually stored as a dry powder and reconstituted with an aqueous diluent before administration. Drug release from a microsphere is controlled by drug diffusion and polymer erosion. Microspheres can be administered by SC or IM injection for systemic or local effect.

Dosage: 0.01-100 mg, SC or IM injections, Once/week or Once/3 days, Once/3 months, Once/6 months.

In Vivo Gelling Liquid Polymeric Systems

In a liquid polymeric system, drug is dissolved or dispersed in a solution consisting of the polymer and solvent(s). Compound A can be incorporated in the polymer solution as a ready-to-use product or dispersed in the polymer solution prior to injection. Upon IM or SC injection, the liquid product quickly gels or solidifies to form a depot at the injection site. The gelling of the polymer solution is caused by either the leaching of the solvent(s) or a reversible thermal gelling effect. These liquid polymer systems can be formed by dissolving PLGA copolymers in organic solvents (i.e., N-methylpyrrolidone and benzyl benzoate) or by dissolving PLGA-PEG block polymers in an aqueous medium. The release of drug from the in-situ depot is mainly controlled by drug diffusion and polymer erosion.

Dosage: 0.01-100 mg, SC or IM injections, Once/week or Once/3 days, Once/3 months, Once/6 months.

In Vivo Gelling Liquid Systems

Sucrose acetate isobutyrate (SAIB) is a highly viscous material which forms a low viscosity solution in a water miscible organic solvent (i.e., ethanol). Compound A can be dissolved or disperesed in a SAIB solution to yield an injectable liquid (SABER®). Upon IM/SC injection, the leaching of the solvent will result in the formation of a depot. The sustained release of the drug can then be achieved by drug diffusion through the gelled SAIB matrix which is undergoing biodegradation.

Dosage: 0.01-100 mg, SC or IM injections, Once/week or Once/3 days, Once/3 months, Once/6 months.

Bio-Conjugation Systems

A Drug Affinity Complex (DAC®) is Formed by Conjugating Compound A to an Endogenous protein (i.e. albumin) in vivo. The biological half-life of the drug can be prolonged by the endogenous protein. The final product is administered IV for systemic effect.

Dosage: 0.01-100 mg, SC or IM injections, Once/week or Once/3 days, Once/3 months, Once/6 months.

Microporation Systems

Microporation Systems consist of microneedles which are array of microprojections less than 100 microns in size. These microneedles can create micropores in the stratum corneum layer of the skin to allow passage of drug molecules without causing bleeding. This approaches is applicable to drugs which cannot be delivered by passive transdermal patches, in particular hydrophilic drugs with a high molecular weight. However, the dose that can be delivered using this technology is still low (<10 mg). Two microneedle configurations are available: A) hollow microneedles, in which the drug reservoir is placed above needle array, and B) microprojections, which are solid (not hollow) and the drug is coated onto the projections on the bottom side of the array.

Dosage: 0.01-100 mg, SC or IM injections, Once/week or Once/3 days, Once/3 months, Once/6 months.

Transdermal

Drug-in-Adhesive Patches

Adhesive patches are the simplest patches to be manufactured. Drugs are dissolved in an adhesive and applied to a backing Dosage: 0.01-100 mg, SC or IM injections, Once/week or Once/3 days, Once/3 months, Once/6 months.

Reservoir Patch

Drug is dissolved or suspended in a compartment above a membrane, and may contain enhancers in the reservoir. These patches are bulkier than drug-in-adhesive and matrix patches, but may afford higher permeability and drug load.

Dosage: 0.01-100 mg, SC or IM injections, Once/week or Once/3 days, Once/3 months, Once/6 months.

Matrix Patch

Matrix patches are composed of several laminates, e.g., drug layer, permeable membrane, and adhesive layer.

Dosage: 0.01-100 mg, SC or IM injections, Once/week or Once/3 days, Once/3 months, Once/6 months.

Energized Transdermal Systems

Poration technologies Poration technologies are applied to create transient channels in the skin for the passage of drug molecules. Electrical potential (electroporation), ultra sound (sonophoresis), and radio frequency radiation (R.P. poration) can be used to generate the transitory structural perturbation of lipid bilayer membranes allowing molecular transport of drugs through the transiently permeabilized skin Electoroporation, Sonophoresis and Radio Frequency Poration.

Dosage: 0.01-100 mg, Poration device, Once/week or Once/3 days, Once/3 months, Once/6 months.

Oral Matrix System

Drug is uniformly dispersed or dissolved in the polymer or a mixture of polymers such as hydroxypropylmethyl cellulose (HPMC), hydroxypropyl cellulose (HPC), methyl cellulose, other cellulosic polymers, polyvinyl pyrrolidone (PVP), and xanthan gum. The drug-polymer matrix is produced by direct compression, granulation or melt-extrusion. The rate of drug availability is controlled by the rate of erosion and diffusion of the tablet.

Dosage: 0.01-100 mg, Tablets, mini tablets or pellets filled in a hard gelatin capsule, Once/week or Once/3 days, Once/3 months, Once/6 months.

Membrane Controlled System

In barrier film or membrane based modified release systems, immediate release drug core or reservoir is coated with a rate controlling polymeric membrane. Water insoluble polymers commonly used in this system are ethylcellulose and Eudragit. Following ingestion, fluid in the stomach and intestine diffuses through the barrier film into the drug core and dissolves the drug. The diffusion rate through the barrier depends on the thickness and physical properties of the film. The rate-controlling barrier can be applied either onto drug pellets or whole tablets. However, the pellet-based technologies provide easier formulation for dose proportionality when formulated in hard gelatin capsules, less dependent of gastric motility and has minimal food effect leading to lower inter-subject variation of plasma levels.

Dosage: 0.01-100 mg, Tablets, mini tablets or pellets filled in a hard gelatin capsule, Once/week or Once/3 days, Once/3 months, Once/6 months.

Osmotic System

Oral controlled release system (Osmotic System) utilizes the principles of osmotic pressure for the controlled delivery of active agent. The release of drug from the osmotic pump system is governed by factors such as solubility and osmotic pressure of the core components, membrane nature, and size of the delivery orifice. The release rate is independent of the physiological factors of the GI tract to a large extent. These systems are amenable to delivery drugs of diversified nature at a pre-programmed rate. The manufacture of osmotic system is more costly and complex than those of matrix system and membrane controlled systems.

Dosage: 0.01-100 mg, Tablets, mini tablets or pellets filled in a hard gelatin capsule, Once/week or Once/3 days, Once/3 months, Once/6 months.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably, the nAChR ligands are administered orally The methods of the invention provide administering nAChR ligands in doses previously not expected to have a pharmacological effect. The lower dosages of the present invention stem from the unexpected potency and extended effect of the nAChR ligands of Formulas (I-V).

It is understood that the foregoing detailed description and accompanying examples are merely illustrative and are not to be taken as limitations upon the scope of the invention, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Methods of the Present Invention

The present invention provides methods for the prevention and treatment of diseases and conditions that are mediated by nicotinic acetylcholine receptors in mammals. In an embodiment, the mammal is a human.

An embodiment relates to ligands of $\alpha 7$-containing neuronal nicotinic acetylcholine receptors (nAChRs), $\alpha 4\beta 2$ nAChRs, or both $\alpha 7$ and $\alpha 4\beta 2$ nAChRs, a therapeutically suitable salt, prodrug, or a metabolite thereof, for the prevention and treatment of diseases and conditions that are mediated by neuronal nicotinic acetylcholine receptors, and methods of use thereof.

Another embodiment is a method of administering a pharmaceutically effective amount of ligands of $\alpha 7$-containing neuronal nicotinic acetylcholine receptors (nAChRs), $\alpha 4\beta 2$ nAChRs, or both $\alpha 7$ and $\alpha 4\beta 2$ nAChRs, a therapeutically suitable salt, prodrug, or a metabolite thereof, to a mammal in need thereof.

Another embodiment is a unit dosage according to a continuous schedule having a dosing interval selected from the group consisting of once-daily dosing, once-weekly dosing, twice-weekly dosing, biweekly dosing, and twice-monthly dosing. Other embodiments relate to methods comprising a continuous dosing schedule having a dosing periodicity ranging from about once every 3 days to about once every 16 days. In another embodiment, the dosage comprises ligands of $\alpha 7$-containing neuronal nicotinic acetylcholine receptors (nAChRs), $\alpha 4\beta 2$ nAChRs, or both $\alpha 7$ and $\alpha 4\beta 2$ nAChRs in a therapeutically effective amount of from about 0.01 mg to about 250 mg.

Another embodiment is a method for treating or preventing a condition or disorder modulated by an $\alpha 7$ nicotinic acetylcholine receptor, wherein the condition or disorder is selected from attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain and inflammatory pain.

Another embodiment is a method for treating or preventing a condition or disorder modulated by an α7 nicotinic acetylcholine receptor, wherein the condition or disorder is schizophrenia.

Another embodiment is a method for treating or preventing a condition or disorder modulated by an α7 nicotinic acetylcholine receptor in combination with an atypical antipsychotic.

Another embodiment is a method for treating or preventing a condition or disorder modulated by an α7 nicotinic acetylcholine receptor, wherein the condition or disorder is infertility, lack of circulation, need for new blood vessel growth associated with wound healing, more particularly circulation around a vascular occlusion, need for new blood vessel growth associated with vascularization of skin grafts, ischemia, inflammation, particularly those associated with rheumatoid arthritis, wound healing, and other complications associated with diabetes.

Another embodiment is a method for treating or preventing a condition or disorder modulated both by α7 and α4β2 nicotinic acetylcholine receptors, wherein the condition or disorder is selected from a group of disorders where both α7 and α4β2 nicotinic receptors are implicated. These include attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, inflammation, arthritis of various types, smoking cessation, nicotinic withdrawal syndrome, traumatic brain injury, acute pain, post-surgical pain, osteoarthritic pain, neuropathic and inflammatory chronic pain states.

The present invention comprises a continuous dosing schedule whereby a unit dosage of a nAChR ligand is regularly administered according to a dosing interval selected from the group consisting of once-daily dosing, once-weekly dosing, twice-weekly dosing, biweekly dosing, and twice monthly dosing.

By once-daily ("QD") dosing is meant that a unit dosage of the nAChR ligand is administered once a day, i.e. one time during a twenty-four hour period, preferably at the same time of each day. In the once-daily dosing regimen, the unit dosage is preferably administered about every twenty-four hours. A non-limiting example once-daily regimen would entail the administration of a nAChR ligand every day at seven in the morning.

By once-weekly ("QW") dosing is meant that a unit dosage of a nAChR ligand is administered once a week, i.e. one time during a seven day period, preferably on the same day of each week. In the once-weekly dosing regimen, the unit dosage is generally administered about every seven days. A nonlimiting example of a once-weekly dosing regimen would entail the administration of a unit dosage of the nAChR ligand every Sunday.

It is preferred that the unit dosage is not administered on consecutive days, but the once-weekly dosing regimen can include a dosing regimen in which unit dosages are administered on two consecutive days falling within two different weekly periods.

By twice-weekly ("Q2W") dosing is meant that a unit dosage is administered twice a week, i.e. two times during a seven day period, preferably on the same two days of each weekly period. In the twice-weekly dosing regimen, each unit dosage is generally administered about every three to four days. A nonlimiting example of a twice-weekly dosing regimen would entail the administration of a unit dosage of the nAChR ligand every Sunday and Wednesday. It is preferred that the unit dosages are not administered on the same or consecutive days, but the twice-weekly dosing regimen can include a dosing regimen in which unit dosages are administered on two consecutive days within a weekly period or different weekly periods.

By biweekly dosing is meant that a unit dosage of the nAChR ligand is administered once during a two week period, i.e. one time during a fourteen day period, preferably on the same day during each two week period. In the twice-weekly dosing regimen, each unit dosage is generally administered about every fourteen days. A nonlimiting example of a biweekly dosing regimen would entail the administration of a unit dosage of the nAChR ligand every other Sunday. It is preferred that the unit dosage is not administered on consecutive days, but the biweekly dosing regimen can include a dosing regimen in which the unit dosage is administered on two consecutive days within two different biweekly periods.

By twice-monthly dosing is meant that a unit dosage of the nAChR ligand is administered twice, i.e. two times, during a monthly calendar period. With the twice-monthly regimen, the doses are preferably given on the same two dates of each month. In the twice-monthly dosing regimen, each unit dosage is generally administered about every fourteen to sixteen days. A nonlimiting example of a biweekly dosing regimen would entail dosing on or about the first of the month and on or about the fifteenth, i.e. the midway point, of the month. It is preferred that the unit dosages are not administered on the same or consecutive days but the twice-monthly dosing regimen can include a dosing regimen in which the unit dosages are administered on two consecutive days within a monthly period, or different monthly periods.

The twice-monthly regimen is distinct from, and not encompassing, the biweekly dosing regimen because the two regimens have a different periodicity and result in the administration of different numbers of dosages over long periods of time. For example, over a one year period, a total of about twenty four dosages would be administered according to the twice-monthly regimen (because there are twelve calendar months in a year), whereas a total of about twenty six dosages would be administered according to the biweekly dosing regimen (because there are about fifty-two weeks in a year).

In further embodiments or descriptions of the present invention, the unit dosage is given with a periodicity ranging from about once every 3 days to about once every 16 days. The methods and compositions of the present invention are useful for the prevention or treatment of diseases and conditions that are mediated by nicotinic acetylcholine receptors, such conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's disease, dementia associated with Lewy bodies, dementia associated with Down's syndrome, schizophrenia, smoking cessation, nicotinic withdrawal syndrome, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

Certain aspects of the invention are described in greater detail in the non-limiting Examples that follow:

EXAMPLE 1

Clinical Study A: Experimental Details

Subjects

A Phase 2a proof-of-concept (POC) study in subjects with mild-to-moderate dementia of Alzheimer type was conducted. The study was a randomized, double-blind, placebo- and active-controlled, multicenter study designed to evaluate the efficacy and safety of Compound A (ABT-126) in subjects diagnosed with mild-to-moderate Alzheimer's disease, defined as meeting National Institute of Neurological and Communicative Disorders and Stroke/Alzheimer's Disease and Related Disorders Association (NINCDS/ADRDA) criteria for probable AD. Subjects (N=274) between 55 to 90 years of age who had a score of 10 to 24 on the Mini-Mental Status Examination (MMSE) were enrolled in the study. Subjects were randomized in an equal ratio to one of four treatment groups (placebo, 5 mg Compound A, 25 mg Compound A, or donepezil) for a 12-week treatment period. The primary efficacy measure was the Alzheimer's Disease Assessment Scale—cognitive subscale (ADAS-Cog). Subjects were generally in good health and any chronic medical conditions were stable during the time of screening. Subjects were not taking other medication for Alzheimer's disease.

Study Design

The study was a Phase 2, randomized, double-blind, placebo- and active-controlled, multicenter study designed to evaluate the dose-response relationship and safety of two doses of Compound A in subjects diagnosed with mild to moderate AD, defined as meeting NINCDS/ADRDA criteria for probable AD.

The study consisted of a Screening Period of up to 28 days, a 12-week treatment period, and a post-treatment period. The screening period consisted of three visits: Screening Visit 1, Screening Visit 2, and Day −1. Upon completion of Day −1 procedures, eligible subjects were randomized through an Interactive Voice Response/Interactive Web-Based (IVR/IWB) system. Subjects were randomized in an equal ratio to one of four treatment groups (placebo, 5 mg Compound A, 25 mg Compound A, or donepezil).

Inclusion Criteria for the study subjects include:

The subject and caregiver must voluntarily sign and date an informed consent, approved by an Independent Ethics Committee (IEC)/Institutional Review Board (IRB), prior to the initiation of any study-specific procedures, including withdrawal of medications to qualify for the study. If the subject is not fully competent, full informed consent must be obtained from the subject's representative and assent must be obtained from the subject.

The subject is a male or female between the ages of 55 and 90 years, inclusive, at Screening Visit 1.

The subject meets the NINCDS/ADRDA criteria for probable AD.

The subject has a Mini-Mental Status Examination (MMSE) total score of 10 to 24, inclusive, at Screening Visit 1.

The subject has a Cornell Scale for Depression in Dementia (CSDD) score≤10 at Screening Visit 1.

The subject has a Modified Hachinski Ischemic Scale (MHIS) score of ≤4 at Screening Visit 1.

If female, subject must be postmenopausal for at least two years or surgically sterile (e.g., bilateral tubal ligation or salpingectomy, bilateral oophorectomy or hysterectomy).

If male, the subject is surgically sterile (vasectomy), is sexually inactive, or is using a barrier method of birth control (e.g., condom) with spermicidal foam/gel/film/cream/suppository for the duration of the study and for 30 days following the last dose of study drug. However, if the male subject's partner has been postmenopausal for at least two years or is surgically sterile, then use of a barrier method of birth control is not required.

The subject has an identified, reliable, caregiver (e.g., family member, social worker, nurse), who will provide support and ensure compliance with the study medication and procedures and provide accurate information about the subject's status during the study.

The subject and caregiver are fluent in the language used for administration of the rating scales and cognitive tests and have sufficient visual, hearing and graphomotor skills to complete procedures.

The subject has had a computerized tomography (CT) or magnetic resonance imaging (MRI) scan, interpreted by a radiologist or neurologist, within 36 months prior to randomization and after the subject met NINCDS/ADRDA diagnostic criteria for probable AD. The scan must not show evidence for an alternative etiology for dementia.

With the exception of a diagnosis of mild-to-moderate AD and the presence of stable medical conditions, the subject is in general good health, based upon the results of medical history, physical examination, vital signs, laboratory profile, and a 12-lead ECG.

Randomization, Medication Dosing, and Dispensing

Each subject was instructed to take study drug once-daily in the morning for 12 weeks. Subjects randomized to donepezil took 5 mg donepezil QD for the first 4 weeks and began 10 mg donepezil QD at Week 4 through the remainder of the study. The subject and investigator were blinded to the treatment assignment throughout the study.

TABLE 1

Treatment Assignments

| Treatment Group | N | Dose |
|---|---|---|
| A | 65 | Placebo QD |
| B | 65 | 5 mg Coumpond A QD |
| C | 65 | 25 mg Coumpond A QD |
| D | 65 | 10 mg donepezil QD |

Visits and Measurements

Subjects completed 4 visits during the treatment period at Week 2, Week 4, Week 8 and Week 12. Subjects returned to the study site for a follow-up visit approximately 2 weeks after the Week 12 or premature discontinuation visit for a safety evaluation. In addition, study site personnel contacted each subject's caregiver by telephone approximately 30 days after the subject's last dose of study drug to ascertain the subject's safety status.

Endpoints and Measures of Outcome

The primary efficacy measure was the Alzheimer's Disease Assessment Scale-cognitive subscale (ADAS-cog). The ADAS-cog was designed to assess the cognitive impairments most common in AD. The ADAS-cog is a subscale of the ADAS, which focuses on cognitive functioning and memory. Two versions were used in the study: an 11-item version and an expanded (13-item) version. The 11-item version of the ADAS-cog was the primary endpoint measure in this study. ADAS-Cog (13-item) was administered throughout the study and the primary efficacy variable was considered the change from baseline to final evaluation on the ADAS-cog total score (11-item).

The 11-item ADAS-cog includes the following tests: Word Recall, Commands, Constructional Praxis, Naming Objects and Fingers, Ideational Praxis, Orientation, Word Recognition, Remembering Test Instructions, Comprehension of Spoken Language, Spoken Language Ability, and Word Finding Difficulty. The total score of the 11-item ADAS-cog ranges from 0 to 70, with a higher score representing greater impairment.

The 13-item ADAS-cog is comprised of the 11-item ADAS-cog with two additional items (Delayed Word Recall and a Number Cancellation Test) that are designed to assess attention and concentration. The Delayed Word Recall Test (range from 0 to 10) was an addition to the Word Recall Test to enhance sensitivity of the instrument in assessing cognition functioning on patients with mild AD. The Number Cancellation Test (range from 0 to 5) was reliable and sensitive to a broad range of dementia severity, and was recommended as a useful addition to the 11-item ADAS-cog. The total score of the 13-item ADAS-cog ranges from 0 to 85, with a higher score representing greater impairment. The ADAS-cog (13-item) was administered by a certified rater at Screening Visit 1, Screening Visit 2, and Day-1, as well as Weeks 4, 8, and 12 during the study.

Statistical Analysis

The primary efficacy measure was the ADAS-cog (11-item) total score.

The primary efficacy variable was the change from baseline to the final observation on the ADAS-cog (11-item) total score. The primary efficacy analysis was carried out using an ANCOVA model with treatment and study site as the main effects and baseline score as the covariate. The treatment group difference between a Compound A dose group and placebo was tested at a one-sided significance level of 0.050. Type III sum-of-squares was used to generate the Least Square (LS) means of treatment group differences. The LS mean difference between each Compound A dose group and placebo and the two-sided 90% confidence intervals was estimated from the ANCOVA model where data from all treatment groups were included.

A similar testing procedure was conducted to evaluate the treatment group difference between donepezil and placebo on the change from baseline to final observation of the ADAS-cog (11-item) total score.

A mixed-effects, maximum likelihood, repeated measures (MMRM) analysis was performed to evaluate treatment group differences for the change from baseline to Weeks 4, 8 and 12 on the ADAS-cog (11-item) total score using all observed data. The model included fixed effects of treatment, study site, visit, and treatment-by-visit interaction, with baseline score as a covariate, and the baseline-by-visit interaction. The unstructured covariance structure was used to estimate the within subject variance-covariance structure. Satterthwaite's approximation was used to estimate the denominator degrees of freedom, and the Type III sum-of-squares for the Least Square (LS) means was used to estimate treatment group differences. The primary comparison for the repeated measures analysis was the contrast between each Compound A dose, donepezil, and placebo at Week 12. The treatment group differences at Weeks 4 and 8 were also evaluated.

Results

Subject Characteristics and Disposition

Of the 358 subjects screened, 274 were included in the randomized study. Of the patients included, 257 patients completed the study. The disposition of the study subjects is shown in FIG. 1. Baseline characteristics of the patients are shown in Table 2.

TABLE 2

| Characteristic | Overall N = 274 |
| --- | --- |
| Age (years), mean | 73.9 |
| Gender, female, n (%) | 60% |
| Average age at diagnosis | 72.6 years |
| Average age at diagnosis | 1.3 years |
| Mean Mini-Mental State Exam Score | 19 |
| Baseline MMSE ≤ 19 | 49.1% |
| Baseline MMSE ≥ 20 | 51% |
| ADAS-Cog Score | 26.1 |
| Previous medication usage | 40% |
| Acetylcholinesterase inhibitors | 16.6% |
| Memantine | 3.3% |
| Other | 28.8% |

Efficacy and Safety

Evidence for efficacy of the 25 mg dose of Compound A was obtained in this study, though the magnitude of the improvement was slightly less than that observed for the active control (donepezil). Exposure-response analyses of the data indicate a potential for the efficacy of Compound A to improve at higher doses. Both doses of Compound A were generally well tolerated in subjects with AD. The incidence of adverse events was approximately 40% in each treatment group and there was no evidence for a dose-dependent increase in adverse events in the 25 mg group. There were very few serious adverse events in any treatment group and none that were considered by the investigator to be related to Compound A. There were no consistent clinically meaningful changes in vital signs, ECG parameters or laboratory assessments associated with Compound A.

The primary efficacy variable in the study was the change from baseline to the final observation on the ADAS-cog 11-item total score. The primary efficacy analysis was performed with an Analysis of Covariance (ANCOVA) model, using treatment and study site as the main effects and baseline score as the covariate. By this analysis, a trend of lower LS mean changes was noted at the final assessment relative to baseline for both the Compound A 25 mg treatment group (P=0.095) and the donepezil treatment group (P=0.057) compared to placebo, suggesting improvement in cognition. The LS mean change from baseline to the final assessment for the Compound A 5 mg treatment group was similar to placebo. Results of the ANCOVA analysis are summarized in Table 2.

TABLE 2

Analysis of Covariance of Change from Baseline to Final Evaluation for ADAS-cog (11-Item) Total Score

| Treatment Group | N | Observed Mean (SD) Baseline | Observed Mean (SD) Final | LS Mean (SE) of Change | Difference From Placebo LS Mean (SE) of Difference | 90% CI | P values[a] |
|---|---|---|---|---|---|---|---|
| Placebo | 67 | 24.88 (11.59) | 23.95 (12.75) | −0.68 (0.64) | | | |
| Compound A 5 mg | 66 | 25.19 (9.90) | 24.30 (10.50) | −0.76 (0.64) | −0.08 | (−1.56, 1.40) | 0.464 |
| Compound A 25 mg | 67 | 28.63 (10.93) | 26.61 (12.09) | −1.86 (0.64) | −1.19 | (−2.68, 0.31) | 0.095 |
| Donepezil | 65 | 25.54 (10.83) | 23.21 (11.53) | −2.11 (0.65) | −1.43 | (−2.92, 0.06) | 0.057 |

SD = standard deviation; LS = least square; SE = standard error; CI = confidence interval The results of the ADAS-cog (11-item) total score were evaluated in a second analysis for differences at each assessment time point using the MMRM analysis model. Treatment groups were evaluated for change from baseline to Weeks 4, 8, and 12 using the intent-to-treat data set. Results of the analysis are shown in Table 3 below.

TABLE 3

Repeated-Measure Analysis of Change from Baseline to Weeks 4, 8, and 12 for ADAS-cog (11-Item) Total Score

| Visit Treatment | N | Observed Mean (SD) | LS Mean (SE) of Change from Baseline | Difference From Placebo LS Mean (SE) of Difference | 90% CI | P value[a] |
|---|---|---|---|---|---|---|
| Baseline | | | | | | |
| Placebo | 67 | 24.88 (11.59) | | | | |
| Compound A 5 mg | 66 | 25.19 (9.90) | | | | |
| Compound A 25 mg | 67 | 28.63 (10.93) | | | | |
| Donepezil | 65 | 25.54 (10.83) | | | | |
| Change to Week 4 | | | | | | |
| Placebo | 66 | −0.26 (4.05) | −0.10 (0.46) | | | |
| Compound A 5 mg | 64 | −0.36 (4.01) | −0.06 (0.47) | 0.03 (0.65) | (−1.04, 1.10) | 0.519 |
| Compound A 25 mg | 67 | −1.18 (4.29) | −0.94 (0.46) | −0.84 (0.65) | (−1.92, 0.23) | 0.098 |
| Donepezil | 64 | −1.04 (3.53) | −0.78 (0.47) | −0.68 (0.65) | (−1.75, 0.40) | 0.149 |
| Change to Week 8 | | | | | | |
| Placebo | 63 | −0.81 (3.92) | −0.56 (0.58) | | | |
| Compound A 5 mg | 65 | −0.58 (4.83) | −0.49 (0.57) | 0.07 (0.81) | (−1.27, 1.41) | 0.535 |
| Compound A 25 mg | 63 | −1.94 (5.12) | −1.67 (0.58) | −1.11 (0.82) | (−2.47, 0.26) | 0.091 |
| Donepezil | 59 | −1.69 (4.96) | −1.26 (0.59) | −0.70 (0.83) | (−2.06, 0.66) | 0.199 |
| Change to Week 12 | | | | | | |
| Placebo | 64 | −1.11 (5.16) | −0.83 (0.64) | | | |
| Compound A 5 mg | 64 | −1.01 (5.50) | −0.80 (0.64) | 0.03 (0.90) | (−1.46, 1.51) | 0.512 |
| Compound A 25 mg | 62 | −2.12 (5.53) | −1.97 (0.65) | −1.14 (0.91) | (−2.65, 0.37) | 0.107 |
| Donepezil | 60 | −2.91 (4.76) | −2.40 (0.65) | −1.57 (0.91) | (−3.08, −0.07) | 0.043[b] |

[a]One-sided P value from repeated measures model with treatment, site, visit, baseline score, interactions of treatment and visit; baseline score and visit; covariance structure is unstructured.

[b]Statistically significant at the P = 0.05 level.

Note: The ADAS-cog (11-item) total score ranges from 0 to 70; a decreasing score represents improvement from baseline.

Results of this analysis are in general agreement with the ANCOVA analysis. The MMRM results indicated a trend toward statistical significance at Weeks 4 and 8 in cognitive improvement for the Compound A 25 mg treatment group relative to placebo; results at Week 12 are of a similar magnitude and approach a statistically significant trend. Similarly, the donepezil treatment group LS mean difference from placebo decreased, indicating cognitive improvement relative to placebo. The Compound A 5 mg treatment group LS mean difference from placebo did not decrease over the 12 weeks, suggesting no improvement in cognition relative to placebo, by this analysis. ADAS-Cog (11-item) mean change from baseline is shown in FIG. 2.

The results from the ADAS-cog 13-item total score were also analyzed using ANCOVA and MMRM and are provided in Tables 4 and 5, respectively. ADAS-Cog (13-item) mean change from baseline is shown in FIG. 3.

TABLE 4

Analysis of Covariance of Change from Baseline to Final Evaluation for ADAS-cog (13-Item) Total Score

| Treatment Group | N | Observed Mean (SD) Baseline | Observed Mean (SD) Final | LS Mean (SE) of Change | Difference From Placebo LS Mean (SE) of Difference | Difference From Placebo 90% CI | P values[a] |
|---|---|---|---|---|---|---|---|
| Placebo | 65 | 35.53 (12.19) | 34.28 (14.24) | −0.78 (0.74) | | | |
| Compound A 5 mg | 66 | 37.04 (11.32) | 35.92 (12.07) | −0.90 (0.73) | −0.13 (1.03) | (−1.83, 1.58) | 0.451 |
| Compound A 25 mg | 64 | 40.85 (11.99) | 38.08 (13.81) | −2.60 (0.75) | −1.83 (1.05) | (−3.57, −0.09) | 0.042 |
| Donepezil | 64 | 37.44 (12.37) | 33.90 (13.37) | −3.27 (0.74) | −2.49 (1.04) | (−4.21, −0.78) | 0.009 |

TABLE 5

Repeated-Measure Analysis of Change from Baseline to Weeks 4, 8, and 12 for ADAS-cog (13-Item) Total Score

| Visit Treatment | N | Observed Mean (SD) | LS Mean (SE) of Change from Baseline | Difference From Placebo LS Mean (SE) of Difference | Difference From Placebo 90% CI | P value |
|---|---|---|---|---|---|---|
| Baseline | | | | | | |
| Placebo | 65 | 35.53 (12.19) | | | | |
| Compound A 5 mg | 66 | 37.04 (11.32) | | | | |
| Compound A 25 mg | 64 | 40.85 (11.99) | | | | |
| Donepezil | 64 | 37.44 (12.37) | | | | |
| Change to Week 4 | | | | | | |
| Placebo | 65 | −0.23 (4.61) | −0.01 (0.52) | | | |
| Compound A 5 mg | 64 | −0.67 (4.31) | −0.30 (0.52) | −0.30 (0.73) | (−1.51, 0.91) | 0.343 |
| Compound A 25 mg | 63 | −2.38 (4.72) | −2.13 (0.53) | −2.13 (0.75) | (−3.36, −0.89) | 0.002 |
| Donepezil | 63 | −1.84 (3.94) | −1.53 (0.53) | −1.53 (0.74) | (−2.75, −0.31) | 0.020 |
| Change to Week 8 | | | | | | |
| Placebo | 63 | −0.73 (4.65) | −0.36 (0.69) | | | |
| Compound A 5 mg | 65 | −0.76 (5.88) | −0.64 (0.67) | −0.29 (0.95) | (−1.86, 1.29) | 0.382 |
| Compound A 25 mg | 60 | −2.78 (6.05) | −2.42 (0.70) | −2.06 (0.98) | (−3.69, −0.44) | 0.018 |
| Donepezil | 58 | −2.66 (5.48) | −2.20 (0.70) | −1.85 (0.98) | (−3.46, −0.24) | 0.030 |
| Change to Week 12 | | | | | | |
| Placebo | 62 | −1.60 (6.04) | −1.13 (0.75) | | | |
| Compound A 5 mg | 64 | −1.20 (6.36) | −0.99 (0.73) | 0.15 (1.04) | (−1.58, 1.87) | 0.556 |
| Compound A 25 mg | 59 | −2.89 (6.77) | −2.74 (0.77) | −1.61 (1.08) | (−3.38, 0.17) | 0.0.68 |
| Donepezil | 59 | −4.17 (4.94) | −3.61 (0.76) | −2.48 (1.06) | (−4.23, −0.72) | 0.10 |

There were statistically significant relationships between Compound A exposure (AUC) and the change from baseline in ADAS-cog 11 and ADAS-cog 13 scores (p<0.05). The exposure-response relationship indicates that higher doses of Compound A (50 mg QD and 75 mg QD) may demonstrate improved efficacy.

EXAMPLE 2

Clinical Study B: A Randomized, Double-Blind, Placebo- and Active-Controlled Phase 2 Dose-Ranging Study to Evaluate the Efficacy and Safety of Compound A (ABT-126) in Subjects with Mild to Moderate Alzheimer's Disease The study is an efficacy and safety study evaluating a new treatment for subjects with mild to moderate Alzheimer's disease. The study is a Phase 2 study design to evaluate the efficacy and safety of Compound A in approximately 410 adults with mild to moderate Alzheimer's disease. Subjects will be randomized to one of 5 treatment groups (placebo, 25 mg Compound A, 50 mg Compound A, 75 mg Compound A, and donepezil) for a 24-week treatment period.

The Phase 2, randomized, double-blind, placebo- and active-controlled, multicenter study is designed to evaluate the dose-response relationship and safety of three doses of Compound A in subjects diagnosed with mild to moderate Alzheimer's disease, defined as meeting National Institute of Neurological and Communicative Disorders and Stroke/Alzheimer's Disease and Related Disorders Association (NINCDS/ADRDA) criteria for probable Alzheimer's disease. Approximately 410 subjects between 55 to 90 years of age who have a diagnosis of mild to moderate Alzheimer's disease will be eligible to participate in the study.

The study will consist of a Screening Period of up to 28 days, a 24-week treatment period, and a post-treatment period. The screening period will consist of three visits: Screening Visit 1, Screening Visit 2, and Day −1. Upon completion of Day −1 procedures, eligible subjects will be randomized through an Interactive Voice Response/Interactive Web-Based (IVR/IWB) system. The subjects will be enrolled in two parts. In Part 1, up to 350 eligible subjects will be randomized to one of the 5 treatment groups (placebo, 25 mg Compound A, 50 mg Compound A, 75 mg Compound A, donepezil) through a response-adaptive randomization scheme. In Part 2, subjects will be randomized to the selected dose of Compound A and placebo in 1:1 ratio until a total of 100 subjects have been randomized to that Compound A dose group from both parts.

The primary efficacy measure will be the Alzheimer's Disease Assessment Scale-cognitive subscale (ADAS-Cog) with 11 items. The primary efficacy variable will be the change from baseline to Week 24 assessment on the ADAS-Cog 11-item total score while change from baseline to Week 24 on ADAS-Cog 13-item total score will be used as a secondary efficacy variable.

The ADAS-cog (13-item) will be administered by a certified rater at Screening Visit 1, Screening Visit 2, Day −1 and at Weeks 4, 8, 12, 18 and 24 during the study.

Inclusion Criteria for the study subjects include:

The subject and caregiver must voluntarily sign and date an informed consent. If the subject does not have the capacity to provide informed consent, full informed consent must be obtained from the subject's representative and assent must be obtained from the subject. The subject is a male or female between the ages of 55 and 90 years, inclusive, at Screening Visit 1.

The subject meets the National Institute of Neurological and Communicative Disorders and Stroke/Alzheimer's Disease and Related Disorders Association (NINCDS/ADRDA) criteria for probable Alzheimer's disease.

The subject has a Mini-Mental Status Examination (MMSE) total score of 10 to 24, inclusive, at Screening Visit 1.

The subject has a Cornell Scale for Depression in Dementia (CSDD) score≤10 at Screening Visit 1.

The subject has a Modified Hachinski Ischemic Scale (MHIS) score of ≤4 at Screening Visit 1.

With the exception of a diagnosis of mild to moderate Alzheimer's disease and the presence of stable medical conditions, the subject is in general good health, based upon the results of medical history, physical examination, vital signs, laboratory profile, and a 12-lead electrocardiogram (ECG).

The subject has an identified, reliable caregiver who will provide support and ensure compliance with the study medication and procedures, and provide accurate information about the subject's status during the study.

Based on the data available for Compound A, it is anticipated that doses of 25 mg QD, 50 mg QD, and 75 mg QD will demonstrate efficacy in the tested subjects.

EXAMPLE 3

Experimental Details

Clinical Study C: A Randomized, Double-Blind, Placebo-Controlled Study to Evaluate the Efficacy and Safety of Compound A in Subjects with Mild to Moderate Alzheimer's Disease on Stable Doses of Acetylcholinesterase Inhibitors This is a Phase 2 study designed to evaluate the efficacy and safety of two doses of Compound A in approximately 420 subjects with mild-to-moderate Alzheimer's Disease (AD) taking stable doses of acetylcholinesterase inhibitors (AChEIs). Subjects will be randomized to one of three treatment groups (Compound A 25 mg, Compound A 75 mg, or placebo) for a 24-week double-blind treatment period.

The Phase 2, randomized, double-blind, placebo-controlled, multicenter study designed to evaluate the efficacy and safety of two doses of Compound A in subjects diagnosed with mild-to-moderate Alzheimer's disease, defined as meeting National Institute of Neurological and Communicative Disorders and Stroke/Alzheimer's Disease and Related Disorders Association (NINCDS/ADRDA) criteria for probable AD. Subjects must be taking stable doses of acetylcholinesterase inhibitors (AChEIs), donepezil or rivastigmine, for at least 90 days prior to Screening Visit 1. Approximately 420 subjects between 55 to 90 years of age who have a diagnosis of mild-to-moderate AD will be eligible to participate in the study. Approximately 30 sites in several countries will take part in this study.

The study will consist of a screening period of up to 28 days, a 24-week treatment period, and a post-treatment period. The screening period will consist of three visits: Screening Visit 1, Screening Visit 2, and a Day −1 Visit. Screening Visit 1 must take place within 28 days of the Day −1 Visit. Screening Visit 1, Screening Visit 2, and the Day −1 Visit will be separated by at least 7 days.

Upon completion of Day −1 procedures, eligible subjects will be randomized through an Interactive Voice Response/Interactive Web-Based (IVR/IWB) system. Subjects will be randomized to one of the 2 Compound A dose arms or placebo in a 1:1:1 ratio. Each subject will be instructed to take study drug once daily in the morning. The subject and investigator will be blinded to the randomized treatment assignment throughout the Treatment Period. Subjects should adhere to the required study schedule. Visit dates are based on the date of the first dose (Day 1), and should be scheduled accordingly. The Week 2 Visit is scheduled approximately 14 days after Day 1; the Week 4 Visit is scheduled approximately 28 days after Day 1, and so on. During the treatment period and post-treatment period visits and phone contacts should occur within ±3 days of the scheduled date.

The primary efficacy measure will be the Alzheimer's Disease Assessment Scale-cognitive subscale (ADAS-Cog) with 11 items. The primary efficacy variable will be the change from baseline to Week 24 assessment on the ADAS-Cog 11-item total score while change from baseline to Week 24 on ADAS-Cog 13-item total score will be used as a secondary efficacy variable.

The ADAS-cog (13-item) will be administered by a certified rater at at Screening Visit 1, Screening Visit 2, Day −1 and at Weeks 4, 8, 12, 18 and 24 during the study.

Inclusion Criteria for the study subjects include:

The subject and caregiver must voluntarily sign and date an informed consent. If the subject does not have the capacity to provide informed consent, full informed consent must be obtained from the subject's representative and assent must be obtained from the subject.

The subject is a male or female between the ages of 55 and 90 years, inclusive, at Screening Visit 1.

The subject meets the Neurological and Communicative Disorders and Stroke/Alzheimer's Disease and Related Disorders Association (NINCDS/ADRDA) criteria for probable AD.

The subject must be receiving a stable dose of an AChEI (donepezil or rivastigmine) for at least 90 days prior to Screening Visit 1.

The subject has a Mini-Mental Status Examination (MMSE) total score of 12 to 24, inclusive, at Screening Visit 1.

The subject has a Cornell Scale for Depression in Dementia (CSDD) score≤10 at Screening Visit 1.

The subject has a Modified Hachinski Ischemic Scale (MHIS) score of <4 at Screening Visit 1.

With the exception of a diagnosis of mild-to-moderate Alzheimer's disease and the presence of stable medical conditions, the subject is in general good health, based upon the results of medical history, physical examination, vital signs, laboratory profile, and a 12-lead electrocardiogram (ECG).

The subject has an identified, reliable caregiver who will provide support and ensure compliance with the study medication and procedures, and provide accurate information about the subject's status during the study.

Based on the data available for Compound A, it is anticipated that doses of 25 mg QD, 50 mg QD, and 75 mg QD will demonstrate efficacy in the tested subjects.

In summary, Compound A has demonstrated a signal for efficacy in the symptomatic treatment of AD in the Phase 2a study and appears to be well tolerated in subjects with Alzheimer's disease in doses up to 25 mg QD and can be anticipated to demonstrate efficacy in the symptomatic treatment of Alzheimer's disease in 50 mg QD, and 75 mg QD.

It is understood that the foregoing detailed description and accompanying examples are merely illustrative and are not to be taken as limitations upon the scope of the invention, which is defined solely by the appended claims and their equivalents.

What is claimed is:

1. A method for treating Alzheimer's disease or an associated dementia in a subject in need thereof, the method comprising:

(a) administering to the subject in need thereof once a day, an effective dosage of (4s)-4-(5-phenyl-1,3,4-thiadiazol-2-yloxy)-1-azatricyclo[3.3.1.1$^{3,7}$]decane or a salt thereof; and (b) repeating step (a) for at least 12 weeks;

wherein the effective dosage is about 75 mg.

2. The method of claim 1, wherein the effective dosage is about 50 mg.

3. The method of claim 1, wherein the effective dosage is about 25 mg.

4. The method of claim 1, further comprising measuring cognitive ability of the subject by use of the Alzheimer's Disease Assessment Scale-cognitive subscale, wherein the subject's cognitive ability is measured every 4 weeks.

5. The method of claim 1, wherein step (b) is conducted for at least 18 weeks or 24 weeks.

6. The method of claim 5, wherein the effective dosage is about 50 mg.

7. The method of claim 5, wherein the effective dosage is about 25 mg.

8. The method of claim 5, further comprising measuring cognitive ability of the subject by use of the Alzheimer's Disease Assessment Scale-cognitive subscale, wherein the subject's cognitive ability is measured every 4 weeks for 12 weeks, and every 6 weeks thereafter.

* * * * *